(12) United States Patent
Kochavi

(10) Patent No.: US 11,033,319 B2
(45) Date of Patent: Jun. 15, 2021

(54) DEVICE AND METHOD FOR ABLATIVE TREATMENT OF TARGETED AREAS WITHIN A BODY LUMEN

(71) Applicant: Vesica E.K. Therapeutics Ltd., Haifa (IL)

(72) Inventor: Eyal Kochavi, Haifa (IL)

(73) Assignee: Vesica E.K. Therapeutics Ltd., Haifa (IL)

( * ) Notice: Subject to any disclaimer, the term of this patent is extended or adjusted under 35 U.S.C. 154(b) by 117 days.

(21) Appl. No.: 15/531,466

(22) PCT Filed: Nov. 22, 2015

(86) PCT No.: PCT/IL2015/051122
§ 371 (c)(1),
(2) Date: May 30, 2017

(87) PCT Pub. No.: WO2016/088120
PCT Pub. Date: Jun. 9, 2016

(65) Prior Publication Data
US 2017/0265924 A1    Sep. 21, 2017

Related U.S. Application Data

(60) Provisional application No. 62/104,879, filed on Jan. 19, 2015, provisional application No. 62/085,666, filed on Dec. 1, 2014.

(51) Int. Cl.
*A61B 18/02*    (2006.01)
*A61B 18/00*    (2006.01)
(Continued)

(52) U.S. Cl.
CPC .......... *A61B 18/0218* (2013.01); *A61B 2017/00022* (2013.01); *A61B 2018/0022* (2013.01);
(Continued)

(58) Field of Classification Search
CPC .......... A61B 2018/0212–0293; A61B 18/02–18/0218
See application file for complete search history.

(56) References Cited

U.S. PATENT DOCUMENTS 3,712,306 A * 1/1973 Bryne ............... A61B 18/0218
606/22
4,674,499 A * 6/1987 Pao ................... A61B 18/1402
604/20
(Continued)

FOREIGN PATENT DOCUMENTS

EP    2303099    4/2011
ES    2491540    9/2014
(Continued)

OTHER PUBLICATIONS

International Preliminary Report on Patentability dated Jun. 15, 2017 From the No. PCT/IL2015/051122. (7 Pages).
(Continued)

*Primary Examiner* — Daniel W Fowler

(57) ABSTRACT

Disclosed is a cryotherapy device comprising at least one inflow channel, at least one outflow channel, control means for controlling the evacuation of expanded cryo-fluid from a body lumen, wherein the control means receive data from at least one sensor that gathers data regarding at least one parameter of the body lumen and wherein the cryotherapy device is introduced into the body lumen via an endoscope.

20 Claims, 13 Drawing Sheets

(51) Int. Cl.
  *A61B 90/00* (2016.01)
  *A61B 17/00* (2006.01)
(52) U.S. Cl.
  CPC .............. *A61B 2018/00577* (2013.01); *A61B 2018/00642* (2013.01); *A61B 2018/00648* (2013.01); *A61B 2018/00744* (2013.01); *A61B 2018/00791* (2013.01); *A61B 2018/0212* (2013.01); *A61B 2018/0268* (2013.01); *A61B 2090/064* (2016.02)

(56) References Cited

U.S. PATENT DOCUMENTS

| | | | |
|---|---|---|---|
| 5,846,235 | A | 12/1998 | Pasricha et al. |
| 5,902,299 | A * | 5/1999 | Jayaraman ......... A61B 18/0218 |
| | | | 604/101.05 |
| 6,027,499 | A | 2/2000 | Johnston et al. |
| 6,319,248 | B1 * | 11/2001 | Nahon ............... A61B 18/0218 |
| | | | 604/523 |
| 7,220,257 | B1 * | 5/2007 | Lafontaine ............. A61B 18/02 |
| | | | 606/21 |
| 7,758,571 | B2 | 7/2010 | Saadat |
| 8,585,690 | B2 | 11/2013 | Lehmann et al. |
| 8,663,211 | B2 | 3/2014 | Fourkas et al. |
| 9,144,449 | B2 | 9/2015 | Burr et al. |
| 9,820,797 | B2 | 11/2017 | Burr et al. |
| 2003/0060815 | A1 * | 3/2003 | Lalonde ................ A61B 18/02 |
| | | | 606/23 |
| 2004/0024392 | A1 * | 2/2004 | Lewis .................... A61B 18/02 |
| | | | 606/22 |
| 2004/0082943 | A1 * | 4/2004 | Littrup .................. A61B 18/02 |
| | | | 606/21 |
| 2004/0106841 | A1 | 6/2004 | Shaw et al. |
| 2005/0081541 | A1 | 4/2005 | Copping |
| 2006/0135962 | A1 * | 6/2006 | Kick .................. A61B 17/3478 |
| | | | 606/108 |
| 2007/0244353 | A1 | 10/2007 | Larsen |
| 2007/0276360 | A1 | 11/2007 | Johnston et al. |
| 2009/0157002 | A1 | 6/2009 | Dumot et al. |
| 2009/0192504 | A1 | 7/2009 | Askew |
| 2010/0049184 | A1 | 2/2010 | George et al. |
| 2010/0076420 | A1 | 3/2010 | Carter |
| 2010/0100087 | A1 | 4/2010 | Mazzone et al. |
| 2010/0179527 | A1 * | 7/2010 | Watson ................. A61B 18/02 |
| | | | 606/21 |
| 2011/0125143 | A1 | 5/2011 | Gross et al. |
| 2011/0208166 | A1 | 8/2011 | Dumot et al. |
| 2012/0136343 | A1 * | 5/2012 | Burnett ................. A61B 18/04 |
| | | | 606/21 |
| 2012/0143167 | A1 | 6/2012 | Morrison et al. |
| 2012/0265186 | A1 | 10/2012 | Burger et al. |
| 2013/0066308 | A1 | 3/2013 | Landman |
| 2013/0218149 | A1 * | 8/2013 | Braun ................ A61B 1/00082 |
| | | | 606/21 |
| 2013/0289678 | A1 * | 10/2013 | Clark ................. A61B 18/1492 |
| | | | 607/101 |
| 2014/0276577 | A1 | 9/2014 | Thralls |
| 2014/0303551 | A1 * | 10/2014 | Germain ................ A61B 17/22 |
| | | | 604/30 |
| 2014/0309655 | A1 | 10/2014 | Gal et al. |
| 2015/0066005 | A1 | 3/2015 | Fan et al. |
| 2015/0080794 | A1 | 3/2015 | Duong et al. |
| 2015/0148791 | A1 | 5/2015 | Birdsall et al. |
| 2017/0014202 | A1 | 1/2017 | Ransbury et al. |
| 2020/0297403 | A1 | 9/2020 | Kochavi |

FOREIGN PATENT DOCUMENTS

| | | |
|---|---|---|
| GB | 2289413 | 11/1995 |
| WO | WO 98/52479 | 11/1998 |
| WO | WO 2012/006408 | 1/2012 |
| WO | WO 2012/060932 | 5/2012 |
| WO | WO 2013/052634 | 4/2013 |
| WO | WO 2016/088120 | 6/2016 |
| WO | WO 2017/189781 | 11/2017 |
| WO | WO 2018/142411 | 8/2018 |

OTHER PUBLICATIONS

Supplementary European Search Report and the European Search Opinion dated Oct. 5, 2018 From the European Patent Office Re. Application No. 15864429.4. (12 Pages).

Supplementary European Search Report and the European Search Opinion dated Jun. 28, 2018 From the European Patent Office Re. Application No. 15864429.4. (14 Pages).

International Search Report and the Written Opinion dated May 10, 2018 From the International Searching Authority Re. Application No. PCT/IL2018/050124. (20 Pages).

International Search Report and the Written Opinion dated Feb. 28, 2016 From the International Searching Authority Re. Application No. PCT/IL2015/051122. (10 Pages).

International Preliminary Report on Patentability dated Aug. 15, 2019 From the International Bureau of WIPO Re. Application No. PCT/IL2018/050124. (14 Pages).

Supplementary Partial European Search Report and the European Provisional Opinion dated Nov. 3, 2020 From the European Patent Office Re. Application No. 18747862.3. (11 Pages).

Supplementary European Search Report and the European Search Opinion dated Mar. 2, 2021 From the European Patent Office Re. Application No. 18747862.3. (12 Pages).

* cited by examiner

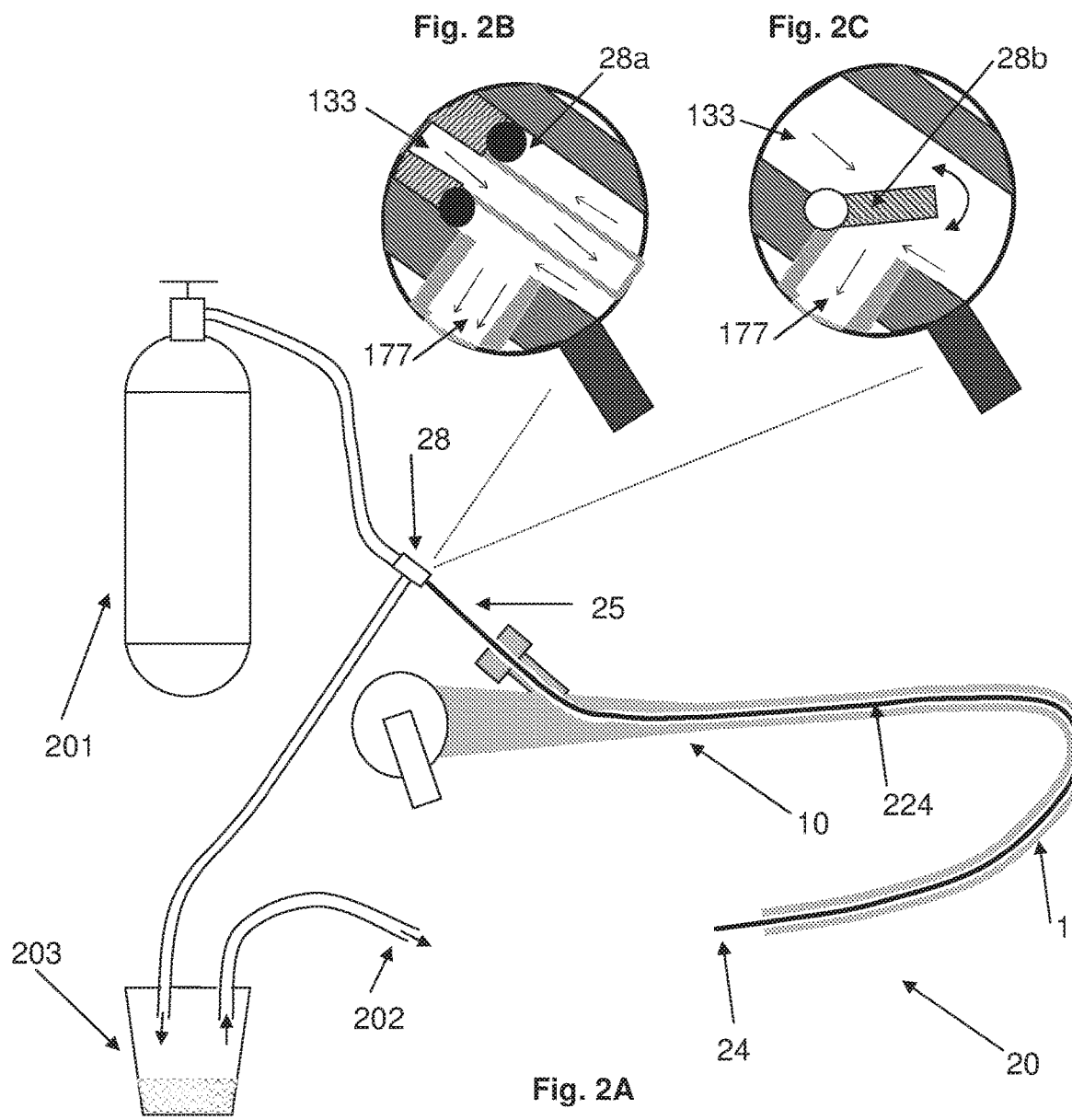

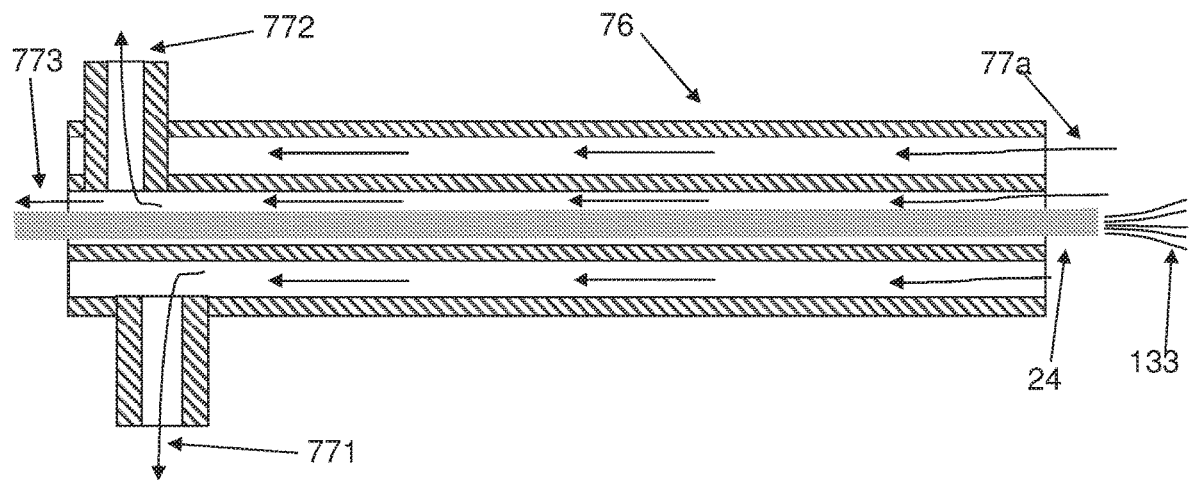
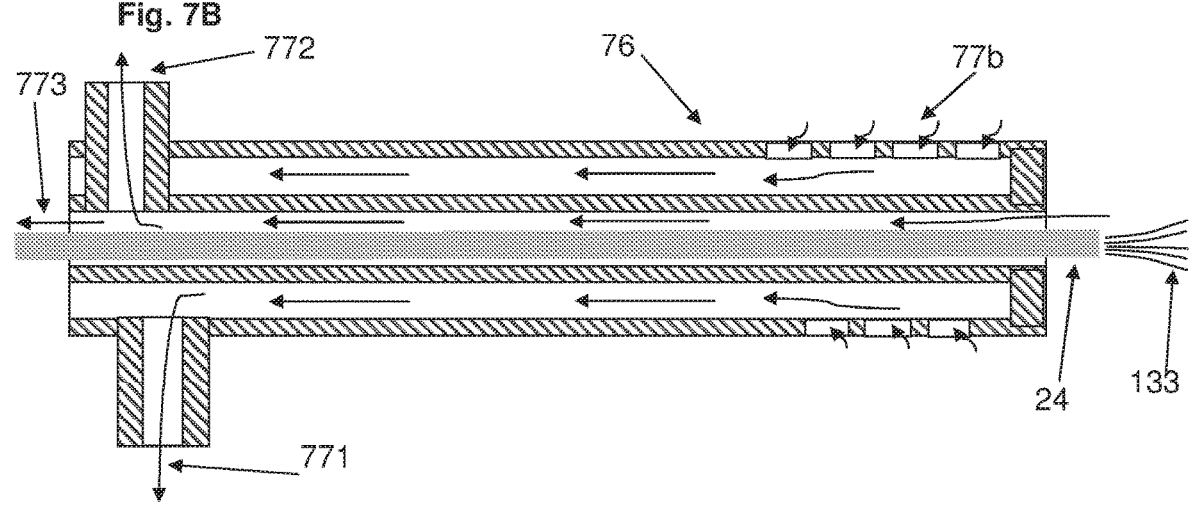

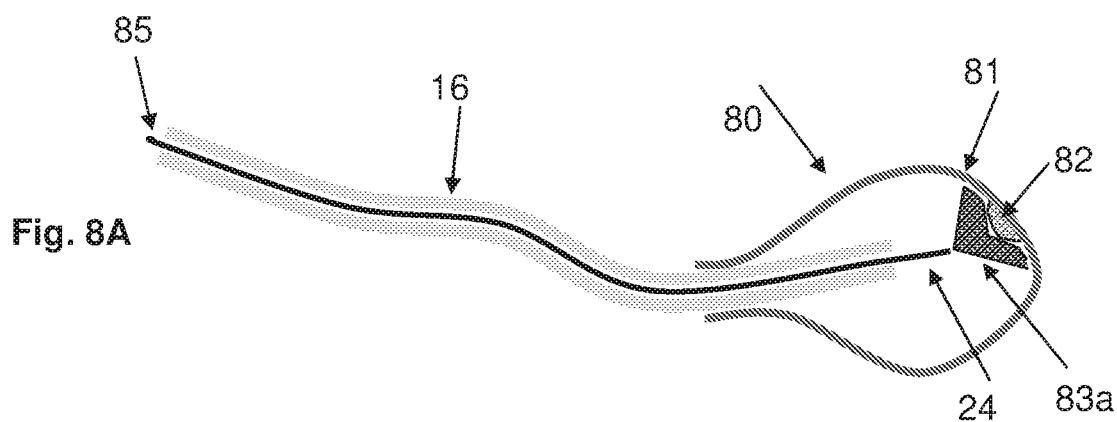
Fig. 8A
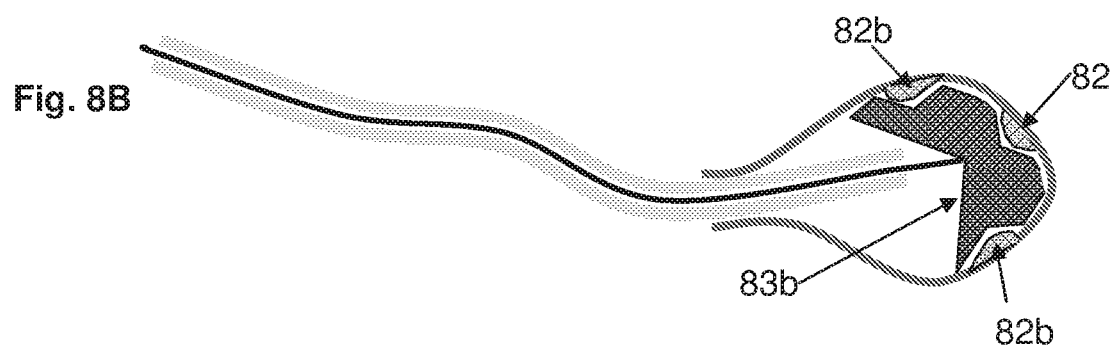
Fig. 8B
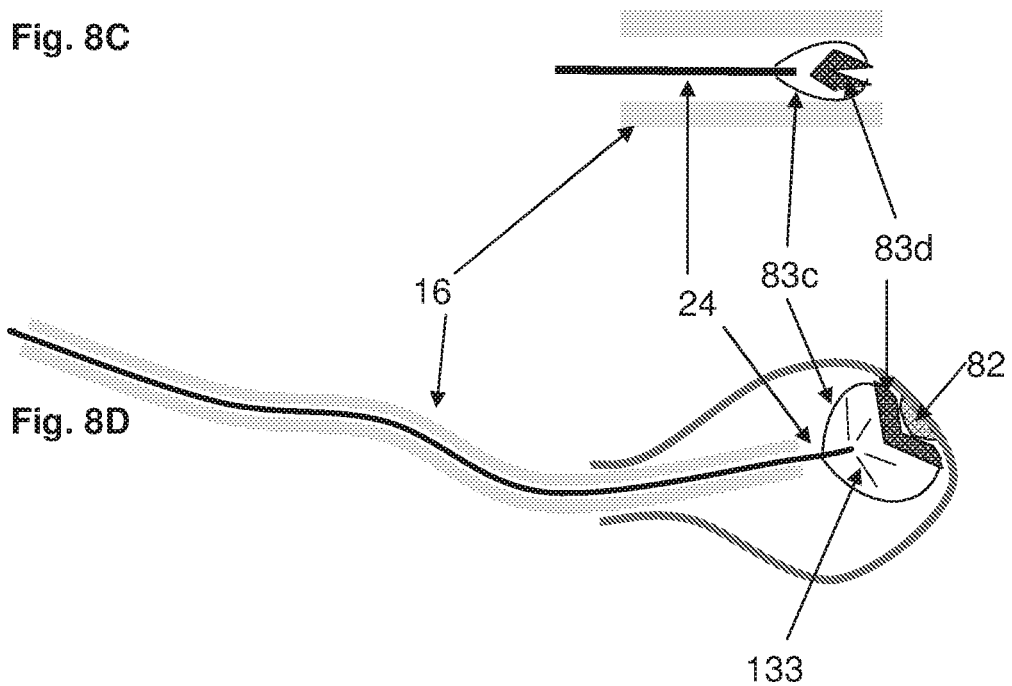
Fig. 8C
Fig. 8D

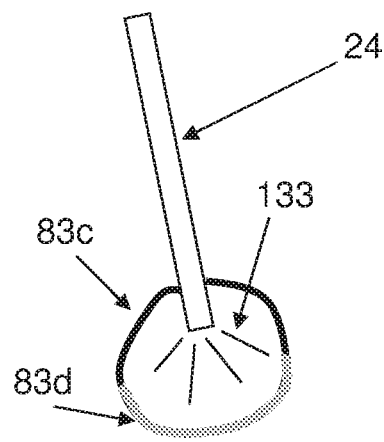
Fig. 8E
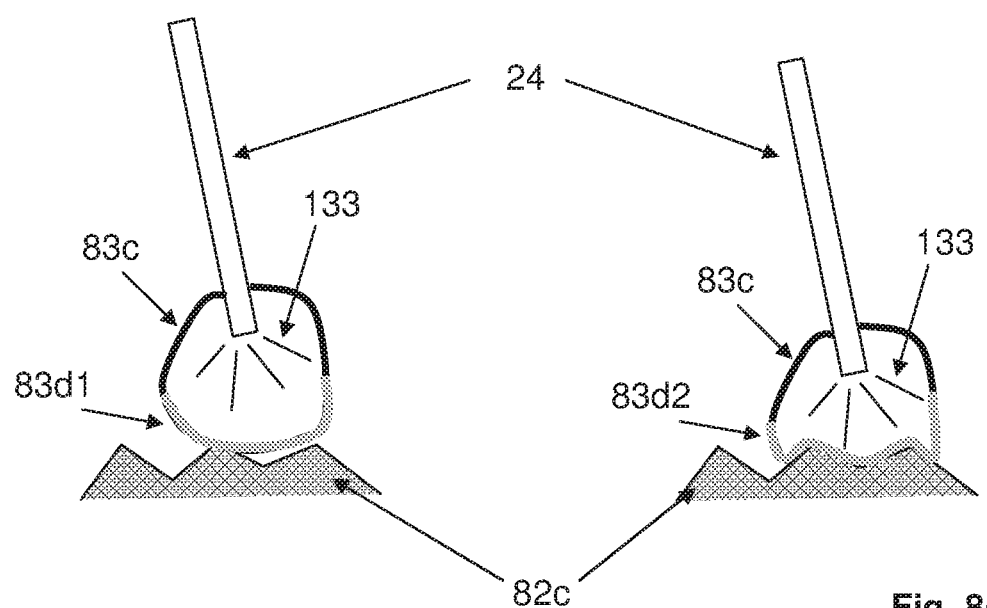
Fig. 8F
Fig. 8G

DEVICE AND METHOD FOR ABLATIVE TREATMENT OF TARGETED AREAS WITHIN A BODY LUMEN

RELATED APPLICATIONS

This application is a National Phase of PCT Patent Application No. PCT/IL2015/051122 having International filing date of Nov. 22, 2015, which claims the benefit of priority under 35 USC § 119(e) of U.S. Provisional Patent Application Nos. 62/104,879 filed on Jan. 19, 2015, and 62/085,666 filed on Dec. 1, 2014. The contents of the above applications are all incorporated by reference as if fully set forth herein in their entirety.

FIELD OF THE INVENTION

The invention is related to the field of ablation, including cryoablation, cryosurgery or cryotherapy devices. Particularly, embodiments of the invention are directed to cryotherapy devices for treating body lumen diseases.

BACKGROUND OF THE INVENTION

Cryoablation, cryosurgery or cryotherapy is a technique by which targeted areas, which may include undesired symptoms, lesions, or tree nerve endings are destroyed or ablated by freezing. Tissue destruction by freezing includes direct injury to cells caused by ice crystal formation, as well as delayed injury that may be caused by apoptosis (regulated cells death) and/or vascular effects. Cryotherapy is performed by utilizing a pressurized coolant (such as $CO_2$, $LN_2$, and/or nitrous oxide), in order to directly spray the cryogenic fluid onto the treated tissue and/or to enable an indirect Joule Thompson effect to occur (using coolants, such as, Argon, Nitrogen and/or Krypton).

Radiofrequency ablation (RFA) is used by applying monopolar or bipolar radiofrequency (RF) energy while creating a contact of an RF antenna and a targeted tissue or lesion.

The use of cryosurgery to ablate tumors is expanding, primarily due to its technical ease and low morbidity rate. A potential secondary advantage to the in situ freezing of malignant diseases is the cryo-immunological response, i.e., the generation of an anti-tumor immune response triggered by the natural absorption of the malignant tissue. Clinical reports suggest that cryoablation may induce a systemic antitumor immune response, which has also been confirmed in animal models.

Body lumens may include bladder, uterus and others. Bladder cancer is one of the most common cancers. When a diagnosis is made at an early stage, the majority of patients diagnosed with bladder cancer have superficial disease and are low grade in nature; others however, are diagnosed at a later stage, which the cancer is more invasive and aggressive so surgical intervention (including cystectomy) may be utilized. Bladder cancer has a high likelihood of recurrence; therefore treatment and follow-up is critical in the prevention of recurrence and progression. It is suggested to use cryotherapy or RFA methods in order to improve treatment for bladder lesions, reduce recurrences and potentially increase bladder preservation rate.

Additional example for bladder illness is Interstitial Cystitis (IC), also known as painful bladder syndrome, a chronic condition of bladder and/or pelvic pain, ranging from mild discomfort to severe pain. Although there is no treatment that reliably eliminates IC, medications and other therapies are offered to relieve pain. For example, Botox injections inside the bladder are thought to block the sensory nerves in the bladder that transmit pain. It is suggested to use cryotherapy or RFA methods, ablating/harming free nerves ending, in order to improve treatment for IC and similar conditions, in order to increase patients' comfort for longer times.

Regarding uterine illnesses and lesions, in order to avoid major surgical intervention, such as, hysterectomy or myomectomy, hysteroscopic procedures may be utilized. Uterine lesions may include sub-mucous fibroids or large polyps or menorrhagia with normal endometria. Additional uterine-related illnesses include thin endometrium and/or Asherman's syndrome (AS), both of which hinder conception. It is suggested to use cryotherapy methods in order to improve treatment for uterine illnesses and lesions thus easing the treatment and potentially increasing uterus preservation rate. Generally, cryotherapy may aid in endometrium rejuvenation and therefore result in an increase in the conception success probability.

There are no known cryotherapy or RFA devices that are inserted into body lumen through an endoscope's working channel. On the other hand, catheter devices that are inserted via an endoscope and are used for treating the gastrointestinal (GI) tract are known in the art. The main differences between current GI devices to those required for body lumens treatments are the size of the necessary insertion cavity (esophagus or colon are significantly bigger in diameter) and the steering effort, which is minimal for current GI applications. For example, some cryotherapy devices include the use of a cryogenic fluid jet, such that the cryogenic fluid or coolant exits through a nozzle and is directly applied onto the tissue in the form of a spray. In such devices, when the operator manipulates the endoscope in order to direct the cryotherapy device to a specific area of interest, no major steering effort is required, since movement of the endoscope back and forth may bring the treated lesion to be in front of the applied spray. In some of the cryotherapy devices that utilize spray, an additional aspiration channel is needed in order to evacuate the spray's expanded fluids thus preventing unwanted lumen inflation or tissue perforation. Such an aspiration channel requires additional space, either within the working channel or outside of the endoscope. In addition the distance of the nozzle front the targeted area is not constant when the cryotherapy catheter is not fixed to the endoscope. As a result, the treatment outcome is not predictable and it may be difficult for the physician to follow the cryosurgery protocol.

There are no known RFA devices that are inserted into body lumen while being applied through endoscope's working channel for bladder or uterus treatments or for any other body lumen treatments. However, there are catheter RFA devices that are manipulated via an endoscope and are used for treating the gastrointestinal (GI) tract. Those RFA devices are wider in size than the endoscope so there is a need to insert the device into the working channel from the distal side of the endoscope resulting in an overall inserted device that is wider than the endoscope. In addition, in order to remove the device one needs to remove the endoscope as well.

There is no known use for cryotherapy devices in combination with immune modulation therapy within a body lumen, either using an endoscope or not.

Therefore, there is a need for a modified endoscopic ablation device (cryotherapy, RFA) that allows ablating tissue within body lumens, wherein the device has the ability to perform sharp angular movements, enabling easy manipulation of the device towards a targeted area with respect to the endoscope through which it passes. There is also a need for a modified cryotherapy device with ability to evacuate coolant expanded fluids through the limited size of the body lumen entrance. There is also a need to improve cryo-immunological methods and to adapt them to cryoablation within a body lumen.

SUMMARY OF THE INVENTION

Embodiments of the invention are directed to a cryotherapy device comprising:
at least one inflow channel;
at least one outflow channel;
control means for controlling the evacuation of expanded cryo-fluid from a body lumen; wherein the control means receive data from at least one sensor that gathers data regarding at least one parameter of the body lumen and wherein the cryotherapy device is introduced into the body lumen via an endoscope.

According to some embodiments, the inflow channel and the outflow channel are the same channel. According to some embodiments, the overall diameter of the inflow channel, the outflow channel and any other channels or devices introduced is between 0.8-9.0 mm. According to some embodiments, wherein at least one tube or catheter is fed through at least one channel, and wherein the tube or catheter is at least partially flexible, bendable, kink resistant or any combination thereof.

According to some embodiments, at least one inflow channel and at least one outflow channel are part of a multi-channel fabricated or extruded tube or catheter. According to some embodiments, the inflow Channel, the outflow channel, or both, are at least partially braided, coiled, or both. According to some embodiments, the inflow channel is attached to at least one inflow nozzle, and wherein the inner diameter of any one of the inflow nozzles is in the range of 0.05-0.3 mm. According to some embodiments, the outflow channel is attached to at least one outflow opening, and wherein the inner diameter of any one of the outflow openings is in the range of 0.5-4.0 mm.

Further embodiments of the invention are directed to a method of treating issue within a body lumen, the method comprising:
introducing a cryotherapy device into a body lumen via an endoscope;
injecting cryo-fluid through at least one inflow channel of the cryotherapy device, directly or indirectly, into the body lumen, such that the cryo-fluid expands, directly or indirectly, in the body lumen thereby freezing at least part of the treated tissue; and
evacuating expanded cryo-fluid, directly or indirectly, through at least one outflow channel of the cryotherapy device, from the body lumen;
wherein the evacuation of the cryo-fluid is controlled by control means receiving data from at least one sensor that gathers data regarding at least one parameter of the body lumen.

According to some embodiments, at least one inflow channel and at least one outflow channel are the same channel, wherein the direction of flow therethrough is controlled by the control means. According to some embodiments, at least one inflow channel and at least one outflow channel are part of a multi-channel fabricated or extruded tube or catheter. According to some embodiments, sharp angular movements of the endoscope do not kink the inflow channel or the outflow channel. According to some embodiments, the inflow channel and the outflow channel are at least partially bendable, flexible or kink-resistant. According to some embodiments, the inflow channel, the outflow channel, or both, are at least partially braided, coiled, or both.

According to some embodiments, the body lumen is a bladder, a cervix, a prostate or a uterus. According to some embodiments, body fluids are evacuated from the body lumen through at least one outflow channel. According to some embodiments, the control means receives parameters regarding the internal pressure in the treated body lumen, the temperature of the treated body lumen, flow rate, flow time, or any combination thereof. According to some embodiments, the cryo-fluid is indirectly injected into the body lumen, wherein it is injected into a folded component. According to some embodiments, the folded component is a cryo-balloon. According to some embodiments, the cryo-fluid is injected into a catheter, wherein the catheter is inserted into the body lumen though does not have an opening into the body lumen, and wherein the expanded cryo-fluid is evacuated from within the catheter.

According to some embodiments, the cryo-fluid is injected together with at least one additional active component. According to some embodiments, the active component is a biological, immunological, chemical, nanoparticle or a chemotherapy entity. According to some embodiments, the active component is selected from mitomycin C, doxorubicin and dendritic cells. According to some embodiments, the cryo-fluid is selected from liquid nitrogen, carbon dioxide ($CO_2$), nitrous oxide ($N_2O$), or any combination thereof.

Further embodiments are directed to a cryotherapy device, which is passed through an endoscope, for treating at least one targeted region within a body lumen, the device comprising:
a folded ablating cryo-balloon;
means for introducing the folded cryo-balloon into a body lumen though an endoscope; and
means to unfold the cryo-balloon inside the body lumen.

According to some embodiments, the cryo balloon has regions that have different degrees of compliance, and wherein a region of the cryo-balloon that is active in transferring cold temperature to the targeted regions, is brought into contact with a targeted region by inflation of the balloon, movements of the balloon, or both inflation and movements of the balloon. According to some embodiments, the cryo-balloon is compliant, semi-compliant, non-compliant, or any combination thereof. According to some embodiments, the diameter or average diameter of the cryo-balloon, when folded is below 2.5 mm.

BRIEF DESCRIPTION OF THE DRAWINGS

The above and other objects and advantages of the invention will be apparent upon consideration of the following detailed description, taken in conjunction with the accompanying drawings, in which the reference characters refer to like parts throughout and in which:

FIGS. 2A, 2B and 2C illustrate schematic lengthwise sectional views of a cryotherapy system, specifically presenting means by which fluids may pass in and out of the treated area in accordance with some embodiments of the present invention;

FIGS. 7A and 7B illustrate schematic lengthwise sectional views of a cryotherapy device introduced via a rigid endoscope and especially the use of endoscope's in-flow and out-flow channels, in accordance with some embodiments of the present invention;

FIGS. 8A and 8B illustrate schematic lengthwise sectional views of a cryotherapy device introduced via an endoscope within the treated lumen during ablation procedure in accordance with some embodiments of the present invention;

FIGS. 8C and 8D illustrate schematic lengthwise sectional views of a cryotherapy inflated device introduced via an endoscope within the treated lumen during an ablation procedure in accordance with some embodiments of the present invention;

FIGS. 8E to 8G illustrate schematic lengthwise sectional views of a cryotherapy inflated device introduced inside lumen during an ablation procedure in accordance with some embodiments of the present invention.

Figure 1A:
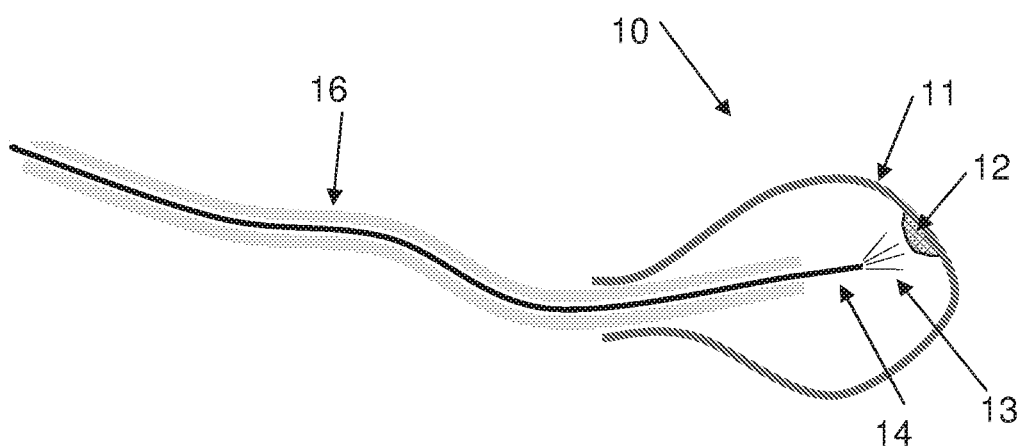
FIGS. 1A to 1D illustrate schematic lengthwise sectional views of a cryotherapy device, during cryotherapy procedure, introduced into the treated lumen via an endoscope in accordance with some embodiments of the present invention.

It will be appreciated that for simplicity and clarity of illustration, elements shown in the figures have not necessarily been drawn to scale. For example, the dimensions of sonic of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Embodiments of the invention are directed to devices and systems for cryotherapy, which may be introduced into a body lumen through an endoscope or any other appropriate means (e.g., inserting a catheter directly into the lumen with no visualization or with outer imaging means, such as an ultrasound, CT and the like). The present invention is further directed to cryotherapy methods within body lumen.

According to some embodiments, the cryotherapy methods include cryo-immunological processes.

It is noted that the term "endoscope" as used herein, is intended to include any type of known endoscope, as well as any type of sheath, catheter, tube or the like, that may be inserted into the body and through which any necessary working channels, optic devices and the like may be placed in the body lumen. Accordingly, the endoscope may include inherent optical means or otherwise, the optical means may be inserted through any type of sheath and the like, such that the optical means may be changed during the procedure, i.e., several different kinds of optics means may be used throughout the procedure. Any other sensors may also be inherent in the endoscope or may be inserted therethrough into the body lumen. It is noted that the term "working channel", or any other equivalent term used herein, may be an integral path through an endoscope or a path available through any means, such as a sheath, catheter, tube or the like, through which any devices and/or sensors, such as optics, may be inserted into the body lumen.

According to some embodiments, the cryotherapy device includes two or more, channels, tubes, catheters, or the like, which allow both the injection of pressurized fluids and the evacuation of expanded fluids, wherein a pressurized fluid is injected into a lumen via at least on channel and the expanded fluid is evacuated from the lumen through at least one second channel. It is noted that catheters, tubes and the like are interchangeably used herein, unless specifically mentioned otherwise. According to some embodiments, at least one injection channel and at least one evacuation channel are inserted into the body lumen via an endoscope. According to some embodiments, the same channel are inserted into the body lumen via an endoscope. According to some embodiments, any channel may pass or be fed through any one of the other channels. According to other embodiments, the same channel may pass or be fed through any one of the other channels. According to the other embodiments, any channel may pass or be fed through any one of the other channels. According to other embodiments, the same channel may be used for both injection and evacuation, using any appropriate type of sensor and/or dedicated algorithm to control flow direction, relative amounts and timing. It is noted that although pressurized and expanded fluid are related to above, any type of fluid may be introduced/released from the system according to any one of the above embodiments. It is noted, as known in the art, the term "fluid" includes both gas and liquid.

Embodiments of the invention further include cryotherapy devices comprising at least one evacuation means as well as control means, by which the evacuation of the expanded fluid, and possibly the injection of the pressurized fluid, are controlled. The control means may be automatic, predefined, electronic, manual, and the like. The cryotherapy device may further include any number or type of sensors, wherein the control means receives data from those sensors and controls the evacuation and/or the injection according to predefined values, according to manual decision, according to values that may change during the process etc. Without such control Means it is possible that pressure would accumulate in the targeted organ, possibly even causing rupture, since the evacuation may not be sufficient. Further, the treated body lumen may have body liquid in it (e.g., urine in the bladder). That body liquid may freeze due to the cryotherapy process, possibly hindering the evacuation of the expended cryo fluid and therefore, it is important to include sensors in the system according to which the control means control the evacuation and possibly the injection, such that the treated lumen is not harmed. According to some embodiments, any number of sensors is inserted into the body lumen. According to some embodiments, any number of external sensors, such as ultra-sound, X-ray and the like may be used together with, or possibly instead of, internal sensors.

According to some embodiments, the inflow may be stopped when the pressure in the lumen is above 30 mBar. According to some embodiments, the outflow evacuation may be continued until the pressure in the lumen is below 20 mBar. According to some embodiments, the inflow may be stopped when the temperature in the lumen is below 10 deg C. According to some embodiments, the inflow may be initiated when the temperature in the lumen is above 15 degC. According to some embodiments, both temperature and pressure, as well as any other appropriate parameters may be used for controlling the system.

Therefore, lumen, such as uterus, pelvis, bladder, kidneys, urethra, and ureters can be treated according to this invention, even though gasses cannot be naturally evacuated therefrom. According to some embodiments, the dynamics of the system, which include both injection of cryo-fluid as well as the evacuation thereof, while monitoring and controlling both the injection and the evacuation during the entire process, prevents liquids or vapors within the lumen from freezing, thus preventing blockage and the like. The combination of the injection, evacuation and control provide the necessary dynamics for the system to operate properly. Further, even lumen having small diameter entrances, such as ureters, may be treated, since the diameter of the injection and evacuation tubes may be relatively small (about 0.8-4 mm overall diameter of all of the tubes together or about 4.0-9.0 mm overall diameter of all of the tubes, particularly if including optics and the like), and further, one tube, or two adjacent tubes, may be used in order to further limit the diameter, since each additional tube used raises the overall diameter. It is noted that small diameters, e.g., about 0.8-9.0 mm overall diameter, may include not only the injection and evacuation channels, but also any other channels, devices, sensors and the like, e.g., optic devices, that are introduced into the body lumen. According to some embodiments, the overall diameter of the inflow and outflow channels is between about 0.8-4.0 mm. The diameter of the outer sheath may be between about 5.0-9.0 mm, and the outer diameter of the optic device is between about 3.0-5.0 mm.

According to some embodiments, bladder, cervix, prostate, urethra, ureter or uterus conditions are treated. According to further embodiments, cancers of the bladder, cervix, prostate, urethra, ureter or uterus are treated. Benign growths may be treated as well. Pain conditions in the bladder, cervix, prostate or uterus may also be treated. According to further embodiments, any type of urinary tract conditions may be treated, including upper tract cancer, interstitial cystitis, bladder pain syndrome, overactive bladder (OAB) and the like.

The distal end of the cryotherapy device may include any number of holes, nozzles, fissures and the like, through which fluids may be injected/introduced/released into the body lumen. According to some embodiments, the fluids may be injected into the lumen together with any additional material, such as chemotherapy, immunotherapy and/or other chemical or biological agents. The additional material may be introduced at the same time, prior to and/or after the cryotherapy treatment for optimal results. The introduced fluid is related to herein also as a "coolant" a "cryo-fluid" and the like. It is noted that the coolant is able to ablate/freeze any desired treated region. According to some embodiments, the distal end of the cryotherapy device includes a nozzle designed for directly spraying fluid onto the targeted area and/or its surroundings. The distal end of the cryotherapy device may further include evacuation means in order to evacuate expanded fluid from a body lumen. According to some embodiments, the cryo-fluid is selected from liquid nitrogen, carbon dioxide ($CO_7$), nitrous oxide ($N_2O$), or any combination thereof. According to some embodiments, the cryo-fluid is selected from argon, nitrogen, krypton or any combination thereof, which may additionally be relevant when the cryo-fluid does not directly contact the body tissue. According to other embodiments, it may further include any additional material, such as chemotherapy, immunotherapy and/or other therapeutics such as chemical or biological agents. According to some embodiments, the additional material is introduced into the body lumen prior to, during and/or after the cryo treatment.

It is noted that the terms "targeted region", "targeted area", "treated region", "treated area", "treated lumen", "targeted lumen" and the like are interchangeable and are intended to include any type of condition that may be treated cryogenically, such as lesions (including cancerous and benign tumors, cysts, polyps and the like), nerves/nerve endings, and various symptoms, even when their specific origin is not fully understood.

According to other embodiments, the coolant remains within the injection channel (e.g., a catheter, tube and the like) and expands therein, so that the cold temperature is transferred into the tissue by a mediating distal section of the cryotherapy device. According to such embodiments, since the coolant remains in the injection channel, there is no need to evacuate the coolant from the body lumen.

According to some embodiments, the mediating distal section of the cryotherapy device is a cryo-balloon, wherein the cryo-balloon is introduced into the treated lumen via an endoscope. The cryo-balloon may be non-compliant, such that it withstands high pressures. If the balloon is non-compliant, the size of the balloon is chosen according to the size of the lumen into which it is inserted or according to shape of a treated area. According to other embodiments, the balloon may be semi-compliant or compliant. According to further embodiments, different sections of the cryo-balloon may have different degrees of compliance. The different parameters of the balloon, including the compliance of the various sections thereof, the shape of the cryo-balloon, the size of the cryo-balloon, etc., may change according to the treated lumen, the targeted area in the lumen, and the like. The balloon may be circular, oval, tubular, or have any flat, or partially flat surfaces. The balloon may also be wide in certain areas and narrow in others, depending on the intended use. When inflated, or partially inflated, the balloon may locally contact only the treated area, not the entire lumen in which the balloon is used. According to other embodiments, the inflation of the cryo-balloon, e.g., in the urethra or ureters, may bring the balloon, or parts thereof, into contact with the entire circumference of the treated area. According to some embodiments, external force, e.g., movements by the user of the device, possibly together with inflation, bring, at least part of the cryo-balloon, into contact with the treated area.

According to some embodiments, the diameter or average diameter of the cryo-balloon, when folded (when inserted through an endoscope or a working channel) is below 2.5 mm. According to some embodiments, the diameter or average diameter of the cryo-balloon, when folded (when inserted through an endoscope or a working channel) is below 2.0 mm. According to some embodiments, the diameter or average diameter of the balloon, when folded (when inserted through an endoscope or a working channel) is below 1.5 mm.

Further, the balloon may be contacted with the targeted area by balloon expansion, partial balloon expansion, and/or by movements of the balloon that may be controlled externally by the user and/or by any appropriate mechanical and/or electronic means. The balloon expansion and/or movements may further be controlled according to data received from any internal or external sensors.

It is noted that the injection and evacuation channels are related to herein also as catheters, tubes and the like.

According to some embodiments, the cryotherapy device may include a flexible or a kink resistant catheter, such as braided or coiled tube, which may allow sharp angular movement, thus enabling targeted areas to be targeted easily regardless of their position within the body.

According to some embodiments, the cryotherapy device includes a single nozzle at the distal end of the device, allowing the operator to perform the treatment within the endoscope's field of view. According to other embodiments, the device includes at least two nozzles, wherein any two nozzles may be positioned in the same or different directions, relative to one another. For instance, any one of the nozzles may be pointed downward, in the distal direction, while other nozzles may be pointed sideways, at any desired angle and distance from the distal end of the device, thereby allowing a multi directional treatment that may treat different parts of the same targeted region, several targeted areas at once, etc. According to some embodiments, one or more of the nozzles has an opened and closed configuration. Further, any one of the nozzles may be partially opened or closed for any time period required. According to some embodiments, any number of nozzles may be electronically controlled, such that the practitioner using the device may use any number of the existing nozzles at any time point, according to the desired treatment. According to some embodiments, the user pre-defines the specific nozzles to be used. According to other embodiments, during the procedure, any one of the nozzles may be opened, partially opened, or closed at any time point, as desired, by any appropriate means, including designated sensors, computerized applications, user commands and the like.

According to some embodiments, a folded component, such as a cryo-balloon may be attached to any part of the distal end of the cryotherapy device. Accordingly, injected cryo-fluid, possibly together with any other appropriate pressure source, inflates the balloon, which in turn freezes at least part of the treated tissue. According to some embodiment, prior to the injection of cryo-fluid, the balloon is inflated by any other appropriate pressure source, allowing the preparation of the balloon for cryo-treatment, checking or testing the system or certain parameters thereof, and the like. The inflation of the balloon, including inflation rate, size etc. may be controlled by any number of sensors, as detailed above regarding the injection through nozzles. Further, any one of the nozzles may be attached on the outside of the nozzle to a cryo-balloon, so that when the cryo-fluid exits the nozzle it inflates the balloon that is attached to the outside of the nozzle.

Thus, according to some embodiments, the cryo-fluid is injected directly into the body lumen, i.e., it comes in direct contact with at least part of the tissue of the body lumen. According to such embodiments, the cryo-fluid is injected directly into the body lumen through any number of nozzles, holes, fissures and/or valves, as detailed herein. Further, if the cryo-fluid is directly injected into the body lumen, it is also directly evacuated therefrom, by any means detailed herein. According to other embodiments, cryo-fluid may be indirectly introduced into the body lumen, such that it does not come in direct contact with the tissue of the body lumen; rather, it is injected into any appropriate component that is positioned inside the body lumen, e.g., a catheter, a cryo-balloon, a tube or the like, which does not include an opening into the body lumen. The cryo-fluid expands within that component, thereby cooling at least part of the treated tissue. The cryo-fluid may then be indirectly evacuated from the body lumen, i.e., it is evacuated from the component into which it was injected. The cryo-fluid may be evacuated by active or passive means.

According to some embodiments, the folded component is a cryo-balloon which is being inflated and/or filled with coolant within the lumen in order to treat the desired area.

According to other embodiments of the current invention, any one of the endoscope's existing 'in-flow' and 'out-flow' channels may be used in order to introduce materials into or evacuate materials from the body lumen (e.g. evacuating cryotherapy expanded fluids).

According to some embodiments, the cryotherapy procedure is performed in combination with any other type of treatment, including intraluminal chemotherapeutic therapy and/or immunotherapy agents. It is noted that the cryo-fluid may be injected together with any other active components. As noted above, the additional active components may be introduced at the same time, prior to, and/or after the cryo-treatment.

The tissue cells that were frozen by the cryo-treatment are removed from the body, inter alia, through the lymph system, wherein an immunological response may be triggered, which may act against such cells in any part of the body, not only the part treated by cryotherapy. According to some embodiments, the introduction of additional active components into the body lumen before or during the cryo-treatment, may cause the treated tissue to react differently to the cryo-treatment, and further, when introduced into the lymph system, the cells together with the additional active ingredient, may cause an enhanced immune response.

The additional active ingredient may be any immunological, chemical, chemotherapeutic, biological or nanoparticle entity, including, though not limited to mitomycin C, doxorubicin, dendritic cells, and the like.

Reference is now made to FIGS. 1A to 1D, which illustrate schematic lengthwise sectional views of embodiments of a cryotherapy device 10 during cryotherapy procedure that is fed into the treated lumen 11 through endoscope 16, As shown in FIG. 1A, jet 13, which may comprise an expanded high pressure cryogenic fluid, is sprayed from distal end 14 of device 10 and is directed at treated region 12, which may be a benign or cancerous tumor, a cyst, a polyp a free nerve ending, or a region in which certain symptoms (pain and the like) occur, even if their specific origin is not known, causing the treated region 12 to be frozen, and thereby, treated or ablated.

Figure 1B:
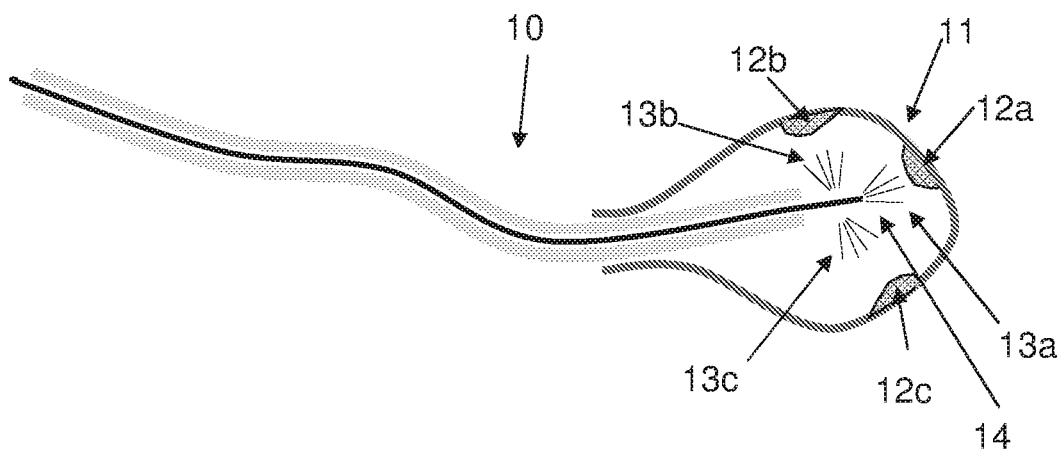

As presented in FIG. 1B, body lumen 11 may include more than one targeted region, e.g., regions 12a, 12b and 12c. Accordingly, the distal end 14 of device 10, may include more than one nozzle (not shown), wherein the jets 13a, 13b and 13c originating from each nozzle are directed at each one of the targeted region. According to some embodiments, the distal end 14 includes numerous nozzles, each of which may have an opened and closed configuration. The nozzles may be utilized, i.e., opened, according to their relative position to the targeted region, such that the nozzles pointing at targeted region are opened and therefore, cryogenic fluid exiting those nozzles is sprayed directly at the targeted regions.

Figure 1C:
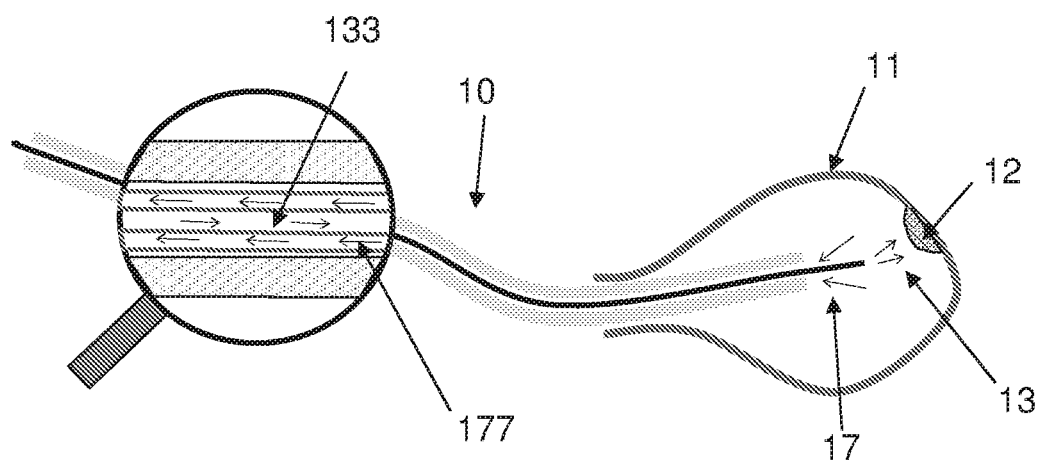

As presented in FIG. 1C, device 10 includes both inflow 133, which provides jet 13 (or any number of jets, as presented in FIG. 1B), and outflow 177, for evacuating, e.g. expanded fluid 17 from lumen 11. The enlarged, portion of device 10 shows that the tube for inflow 133 may be positioned within the tube for outflow 177; however, according to different embodiments, they may be positioned in any relation to one another. In addition, there may be any number of outflow and inflow tubes.

Figure 1D:
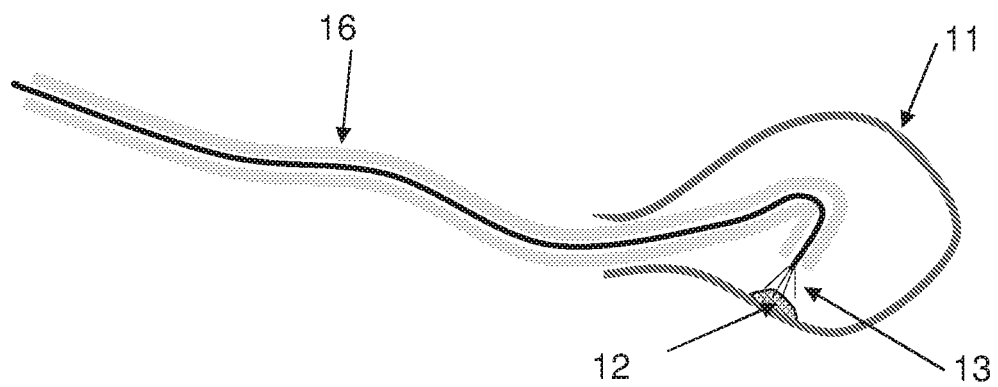

According to some embodiments, and as illustrated in FIG. 1D, endoscope. 16 may be used also at sharp angles, in order for jet 13 to reach treated region 12, no matter where treated region 12 is positioned in body lumen 11

Reference is now made to FIGS. 2A, 2B and 2C, which illustrate schematic lengthwise sectional views of a cryotherapy system, specifically presenting the means by which fluids flow in and out of the treated area in accordance with some embodiments of the present invention. According to some embodiments, cryotherapy system 20 includes a source of pressurized coolant 201 and evacuation means 202. Evacuation means 202 may be dedicated to cryotherapy system 20, general evacuation means, an outlet to the surrounding atmosphere, or any other appropriate means by which material, e.g., expanded fluids, may be evacuated from the system. According to some embodiments, evacuation means 202 includes suction provided by any appropriate pump, vacuum, or the like. According to some embodiments, evacuation means 202 may be attached to the proximal end of cryotherapy device 10. According to some embodiments, the evacuation means 202 are attached to cryotherapy device 10 via junction 28.

According to some embodiments, and as illustrated in FIGS. 2A and 2B, a cryotherapy catheter 224 is inserted into the endoscope 16 such that its distal end 24 reaches the endoscope's distal end while the proximal end of cryotherapy catheter 25 remains outside of the proximal end of endoscope 16. According to some embodiments, proximal end 25 is connected to junction 28 as detailed herein. According to some embodiments of the current invention simultaneous inflow 133 and outflow 177 are allowed (FIG. 2B). Seal 28a may prevent potential Mixture between the two flows. This may be necessary when the two flows are oriented in a coaxial manner inside the endoscope, such that there is a need to separate the flows outside the endoscope. Optional suction trap 203 may collect evacuated fluids and may protect evacuation means 202 from being contaminated.

According to some embodiments, and as illustrated in FIG. 2C, junction 28 includes valve 28b, which controls inflow 133 and outflow 177, such that they do not flow simultaneously; rather, valve 28b determines whether inflow 133 is activated or whether outflow 177 is activated. Valve 28b may be operated according to any appropriate means, including predefined settings, electronic means, manual operation, and the like. Control of valve 28b may take pressure, time, targeted region reaction and the like into account.

According to some embodiments, the inflow may be stopped when the pressure in the lumen is above 30 mBar. According to some embodiments, the outflow evacuation may be continued until the pressure in the lumen is below 20 mBar. According to some embodiments, the inflow may be stopped when the temperature in the lumen is below 10 deg C. According to some embodiments, the inflow may be initiated when the temperature in the lumen is above 15 degC. According to some embodiments, both temperature and pressure, as well as any other appropriate parameters may be used for controlling the system.

According to some embodiments cryotherapy system may include a control mechanism, which controls coolant injection and/or expanded fluid evacuation. The control mechanism may include predetermined parameters (e.g. cyclic) and/or may include parameters defined with feedback to data collected from the system by any appropriate sensors, such as distal pressure, distal temperature, proximal pressure, proximal temperature, comparing flow entered to flow evacuated, operation time and other optional measured parameters. When such feedback related control is implemented, relevant sensing and control means are to be part of the embodiment (like CPU, firmware, flow sensor, pressure sensor, clock, etc.)

Figure 3:
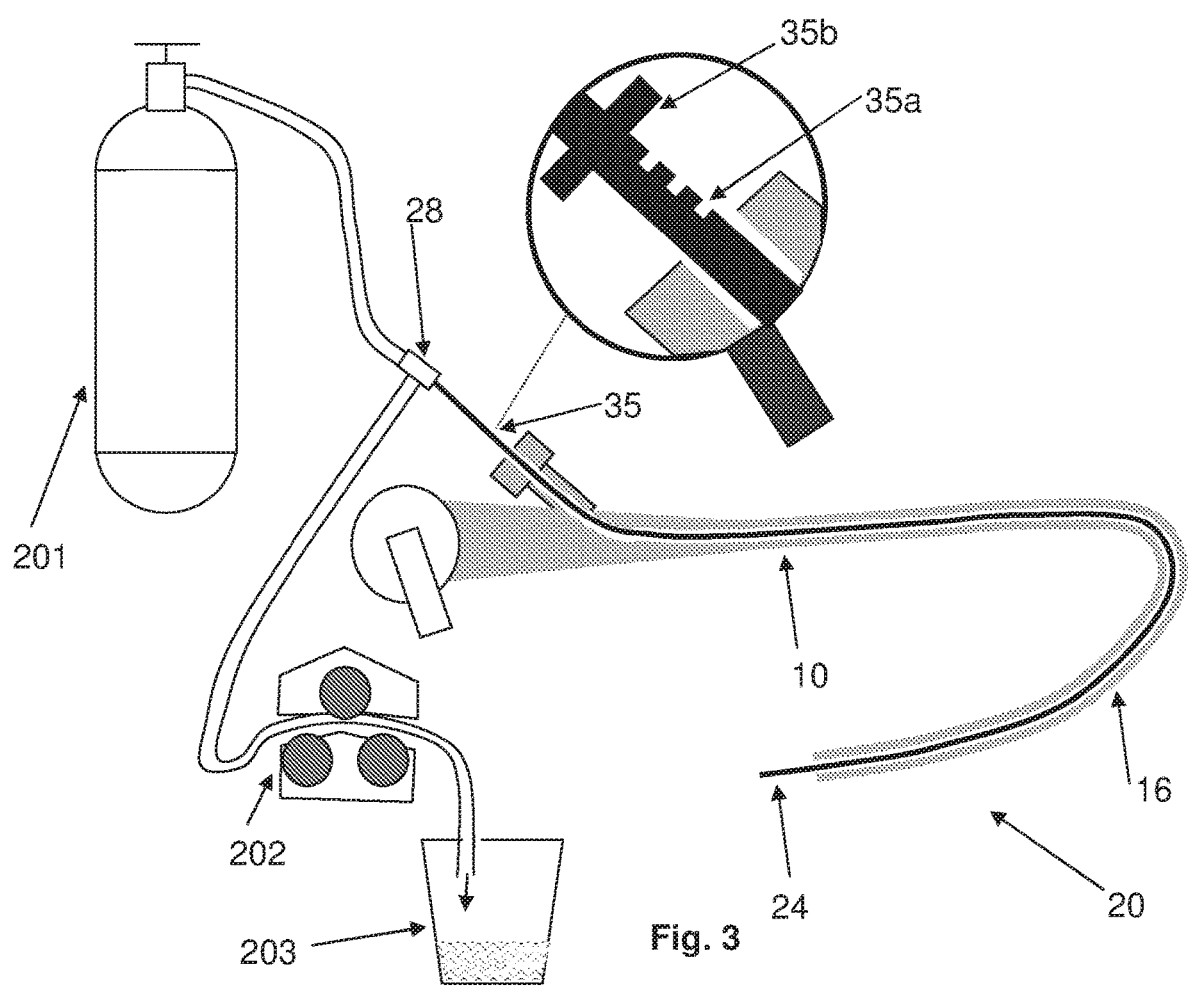
FIG. 3 illustrate a schematic lengthwise sectional view of a cryotherapy system and specifically the means by which the device's distal end is positioned and fixed in accordance with some embodiments of the present invention.

Reference is now made to FIG. 3, which illustrates schematic lengthwise sectional views of an embodiment of the cryotherapy system, specifically the location and possible fixing of the device's distal end. According to some embodiments a cryotherapy system 20 includes a source of pressurized coolant 201 and evacuation means 202, which are mutually connected to proximal end 35 of cryotherapy device 10 at junction 28. Optional suction trap 203 may collect evacuated fluids as required.

According to some embodiments, in order to define the distance between the catheter's distal end 24 from the distal end of endoscope 16, a fixation mechanism is implemented. The fixation means may be attached to proximal end 35 of cryotherapy device 10. Notches 35a provide a specific distance between catheter's distal end 24 from the distal end of endoscope 16 and limiter 35b may be moved and/or fixated according to each specific notch or scale in relation to operator's definition of desired distance. The desired distance may be predefined, controlled by any appropriate electronic means, controlled manually, or the like. The desired distance may be changed during the operation of the device or may be constant throughout the cryotherapy. Limiter 35b may be fixed in a certain notch 35a by any appropriate securing means, such as clips, screws, elastic bands and the like.

Reference is now made to FIGS. 4A to 4D, which illustrate schematic lengthwise sectional views of a cryotherapy device's distal end in accordance with some embodiments of the present invention. It is noted that any number of tubes/catheters may be used both for inflow and outflow in and from the system, respectively. It is further noted that any appropriate configuration of those tubes/catheters in relation to one another is possible, including one inside the other, two adjacent tubes and the like. Some embodiments include a tube/catheter comprising several paths through which fluid may flow in any defined direction. According to some embodiments, distal end 24, comprises paths for the simultaneous flow of pressurized coolant inflow 133, to be sprayed through nozzle 49, and evacuated expanded fluid outflow 177.

Figure 4A:
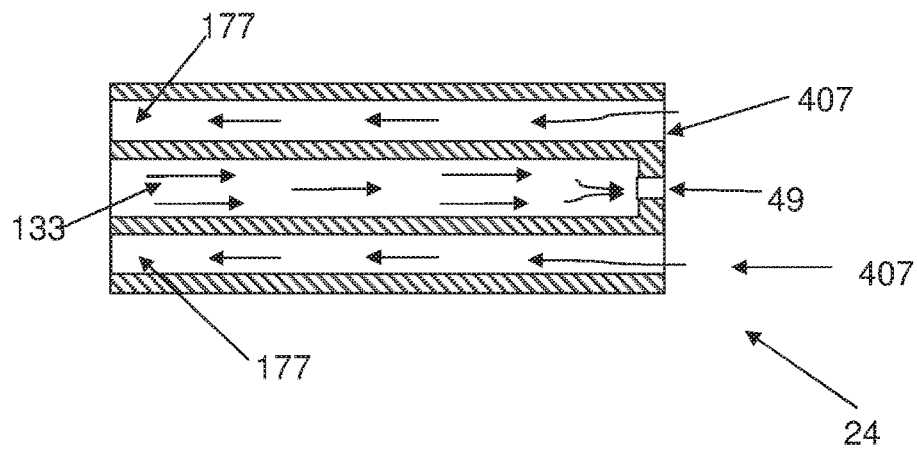
FIGS. 4A to 4E illustrate schematic lengthwise sectional views of a cryotherapy device's distal end in accordance with some embodiments of the present invention.

According to some embodiments, as presented in FIG. 4A, distal end 24 has inflow nozzle 49 and outflow openings 407 in a close or similar plane.

Figure 4B:
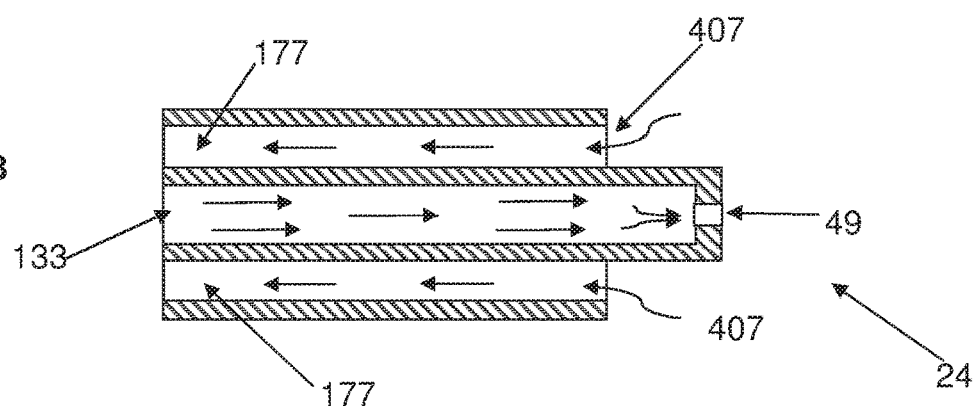

According to other embodiments, as illustrated in FIG. 4B, inflow nozzle 49 and outflow openings 407 are positioned in different planes of distal end 24. When in different planes it is possible that the inflow and outflow do not interfere with one another, thereby optimizing the freezing efficacy of inflow 133 as well as the evacuation of outflow 177.

Figure 4C:
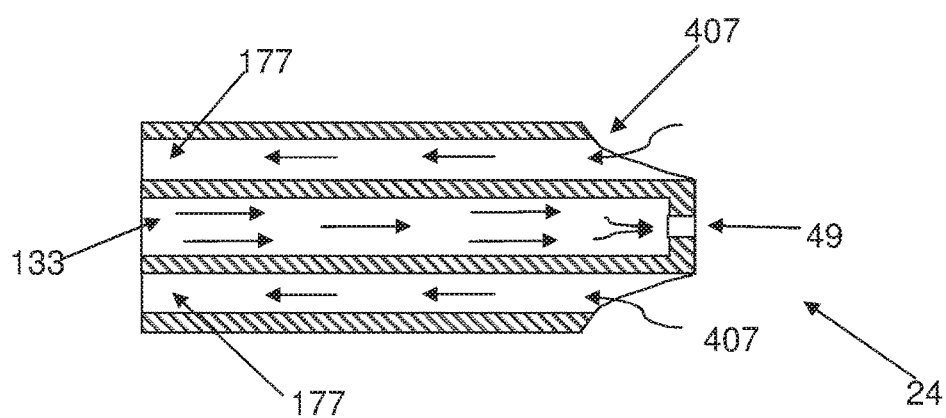

According to other embodiments, as illustrated in FIG. 4C, outflow openings 407 are positioned at a changing distance from inflow nozzle 49, e.g., having an inclined cross-section. This may also provide inflows and outflows that do not interfere with one another. By having a changing distance between inflow nozzle 49 and outflow openings 407, the evacuated fluid passing through outflow openings 407 should not interfere with inflow 133, though is still, at least partially, in close proximity to nozzle 49, such the efficient evacuation/suction of outflow 177 through outflow openings is possible.

Figure 4D:
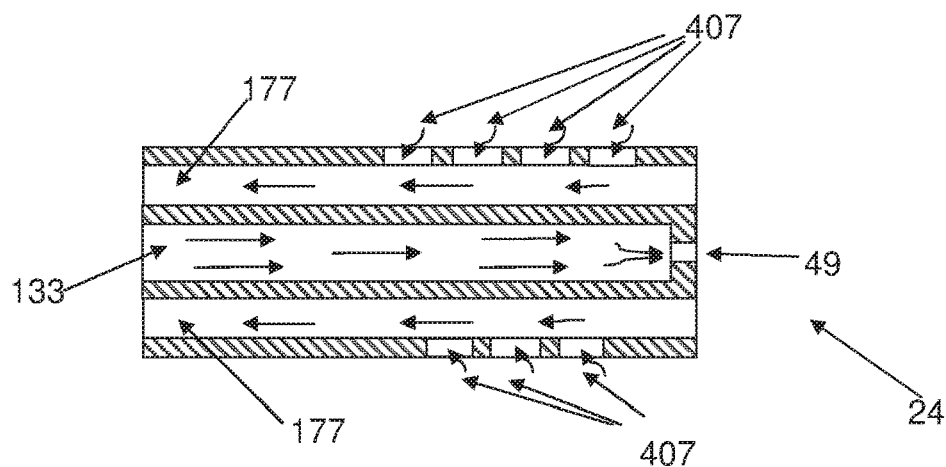

According to other embodiments, as illustrated in FIG. 4D, distal end 24 includes several side outflow openings 407. The side outflow openings 407 may be circumferential or partially circumferential. Utilizing such side openings distances outflow 177 and inflow 133 from one another, such that they do not interfere with one another. Further, since there are several outflow openings 407 they can evacuate fluid efficiently, even though they are positioned on the sides of distal end 24.

Figure 4E:
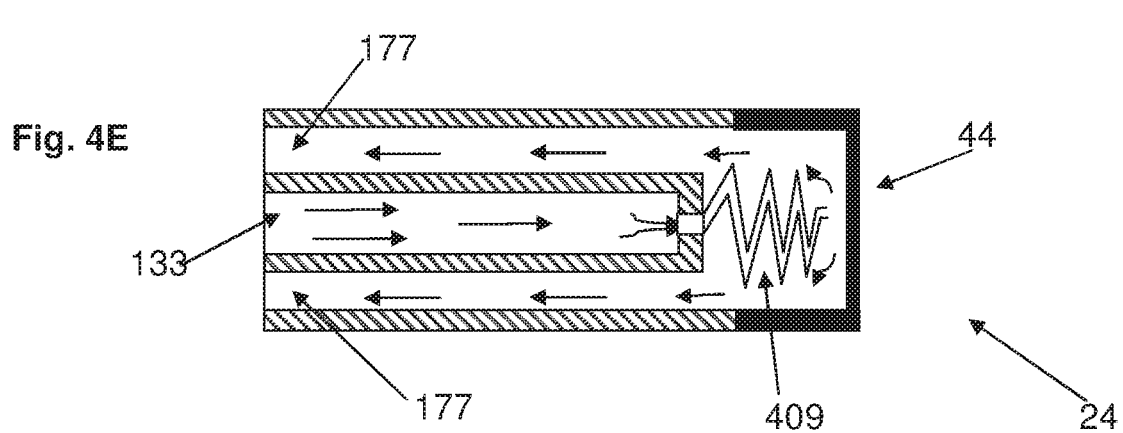

Reference is now made to FIG. 4E, which illustrates schematic lengthwise sectional view of a cryotherapy device's distal end 24 in accordance with another embodiment of the present invention. According to some embodiments, distal end 24 does not comprise any openings into the treated lumen, such that the coolant remains and expands within distal end 24. According to such an embodiment, the transfer of cold temperatures into the tissue is mediated by mediating region 44 of distal end 24. Thus, pressure does not build up in the treated body lumen. According to some embodiments, in order to further optimize temperature drop, i.e., freezing of the treated area, feedback coil 409 may be used for pre-cooling pressurized coolant inflow 133 with the already cooled-expanded fluid of outflow 177.

According to some embodiments, mediating region 44 is prepared from hard material such as stainless steel, copper or brass. According to other embodiments, the mediating region 44 may be at least partially prepared from an expandable or inflatable material, such as a balloon, thereby enabling distal end 24 to assume the geometry of the treated lumen, thereby optimizing the treatment. According to further embodiments, the inflatable/expandable part of mediating region 44 may be inflated/expanded such that it assumes a shape that does not necessarily fill the treated lumen, though is able to touch or surround the targeted region. According to some embodiments, the inflatable/expandable part of mediating region 44 may be inflated/expanded according to predefined parameters, according to signals received from any appropriate sensors, automatically or manually. Further, the rate and size of inflation/expansion may differ throughout the cryotherapy treatment. As detailed above, the mediating region may be prepared from a compliant (15-200%, e.g., prepared from polyurethane, nylon elastomers and other thermoplastic elastomers), non-compliant (0-8%, e.g., prepared from PET, nylon and others) or a semi-compliant material (5-15%, e.g., prepared from polyamides and engineered nylons as polyether block amide (Pebax®), and PET and polyurethane), that may be of any appropriate size and shape and that further may be brought into contact with the treated region by expansion and/or by moving the mediating region, possibly, externally by the user. The expansion and/or the movement may be controlled by any appropriate means and may further be controlled according to data gathered by any internal or external sensors.

Figure 4F:
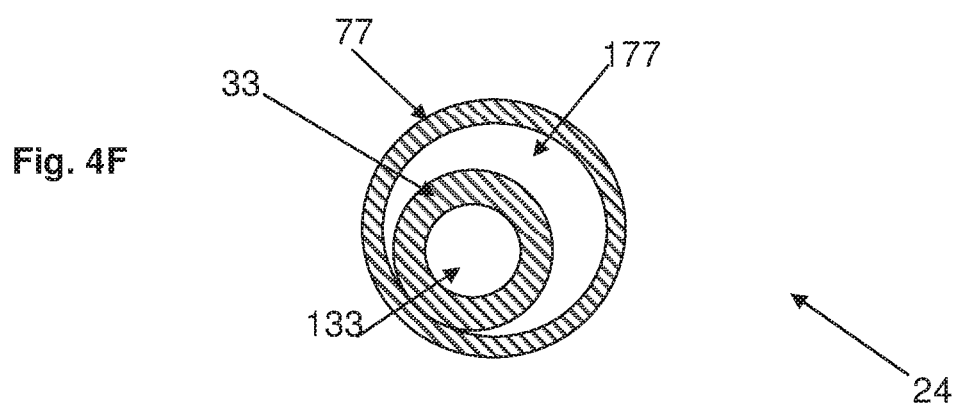
FIGS. 4F to 4H illustrate schematic transverse cross-sectional views of a cryotherapy device's distal end, in accordance with some embodiments of the present invention.
Figure 4G:
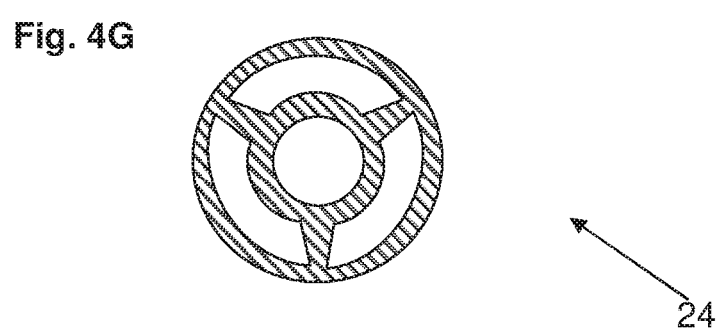
Figure 4H:
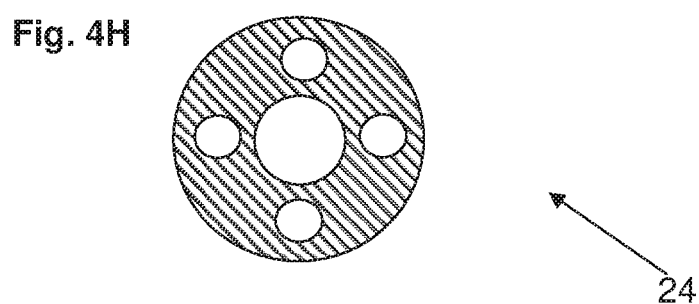

Reference is now made to FIGS. 4F to 4H, which illustrate schematic transverse cross-sectional views of a cryotherapy device. According to some embodiments, inflow 133 flows through tube/catheter 33 that is positioned within tube/catheter 77, through which outflow 177 flows. According to some embodiments, tubes/catheters 33 and 77 may be separate from one another, positioned as desired during or before the cryotherapy treatment. According to other embodiments, tubes/catheters 33 and 77 are integrated together, such that essentially only one such tube/catheter exists, including passageways for both outflow 177 and inflow 133. Thus, two tubes may be used to fabricate the desired shape or otherwise, a tube may be extruded to have the appropriate channels. It is noted that although the embodiment presented in FIG. 4F shows tube 33 within tube 77, according to other embodiments, tube 77 may be placed within or beside tube 33. This is true for the embodiments shown in FIGS. 4G and 4H as well, wherein the position of any of the tubes may be changed according to the system/user requirements. Further, according to some embodiments, the outer tube, in the figure tube 77, may be the endoscope's working channels, through which tube 33 (or vice versa) passes.

According to further embodiments, as presented in FIGS. 4G and 4H, the transverse cross section of distal end 24 has several openings, wherein outflow 177 passes through some of the openings, while inflow 133 passes through other openings. Any one of the openings may serve as an inflow, outflow or a sensing passage, according to the system/user requirements. A sensing passage is one through which at least one sensor passes, wherein data gathered from that sensor may be used to control the system and the use thereof. Further, any one of the passages may serve for either outflow or inflow at different times during the cryotherapy treatment, according to predefined conditions, parameters defined according to data received from any appropriate sensors, electronically or manually. It is noted that although FIGS. 4A-4H present specific embodiments of the distal end of the device, any other embodiments including any number or position of inflow/outflow tubes may be implemented. It is also noted that any such tubes may be prepared from a combination of several tubes, fabrication and/or extrusion.

According to other embodiments, any number of the paths/tubes/catheters passing through endoscope 16 may be used for the sensing means that may be needed for controlling the body lumen pressure or temperature, such as pressure sensing and/or temperature sensing or for any other sensors required. Additional sensing means may include sensors for calculating the lumen's volume (e.g. initial volume and changes in volume due to in and out flows), sensors for sensing the lumen's wall thickness (e.g. by ultrasound or laser light) and the like.

Figure 5A:
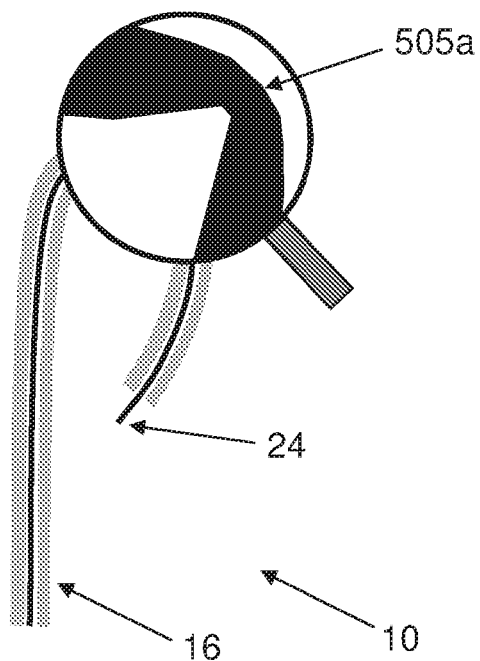
FIGS. 5A to 5D illustrate schematic lengthwise sectional views of a cryotherapy device introduced through an endoscope, during a sharp angulation scenario, in accordance with some embodiments of the present invention.
Figure 5B:
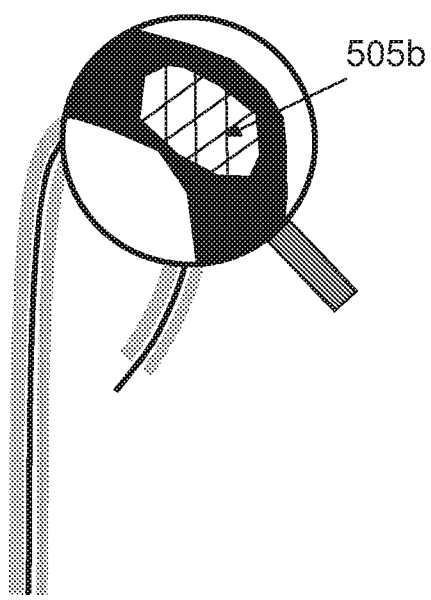
Figure 5C:
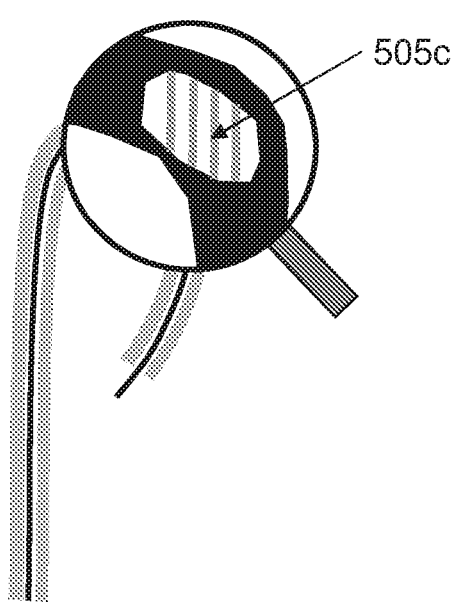
Figure 5D:
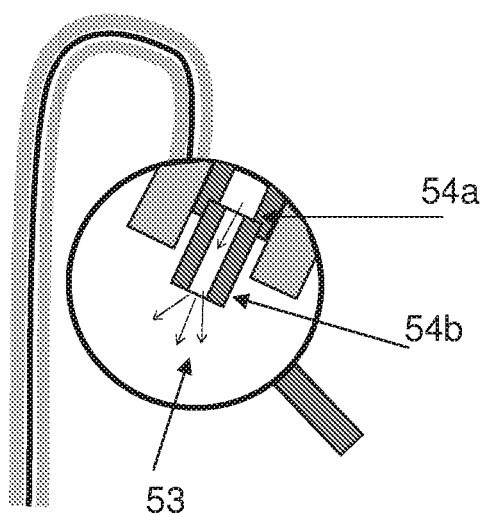

Reference is now made to FIGS. 5A to 5D, which illustrate schematic lengthwise sectional views of a cryotherapy device that is fed into the body lumen via an endoscope during sharp angulation scenario, in accordance with some embodiments of the present invention. According to some embodiments, cryotherapy device 10, which is illustrated in FIG. 5A, is inserted into the working channel of endoscope 16 such that distal end 24 of cryotherapy device 10 reaches the distal end of endoscope 16. When the angulation of endoscope 16, including sharp angulation, is necessary for passing through certain passages and/or for targeting the treated region, it is necessary that no kinks are formed in cryotherapy device 10. Such kinks, for example, kinks 505a, as shown in FIG. 5A, may interfere with the inflow and outflow of fluids through cryotherapy device 10. Accordingly, cryotherapy device 10 may include a tube/catheter that is flexible, bendable and/or kink resistant, such as braided tube 505*b* (FIG. 5B) or coiled tube 505*c* (FIG. 5C), to assist with angulation, including sharp angulation, allowing the targeting of any treated regions throughout the treated lumen, as well as passing through any necessary passageways in order to reach the body lumen. According to some embodiments, cryotherapy device 10 includes a tube/catheter, wherein only certain sections of the tube/catheter are flexible, bendable and/or kink resistant. According to other embodiments, cryotherapy device 10 includes a tube/catheter that is flexible, bendable and/or kink resistant in its entire length.

According to some embodiments, the cryotherapy device may include non-rigid flexible semi-inflatable catheter 54*a* (FIG. 5D) which may be inflated by one of device's flows (pressurized or expanded fluid) up to the working channel geometry. This is especially important when the working channel undergoes angulations. According to some embodiments, a more rigid component 54*b* may be found around the distal end of the catheter (FIG. 5D), such that the rigid components aids in maintaining the orifice shape and direction of the catheter even when expanded, in order to keep the desired sprayed flow 53.

Reference is now made to FIGS. 6A to 6E, which illustrate schematic lengthwise sectional views of a cryotherapy device's distal end, specifically presenting embodiments of nozzles/holes/valves in the inflow tube/catheter and related inflow sprays of cryo-fluid in accordance with some embodiments of the present invention. A cryotherapy device, according to embodiments of the present invention, may comprise a pressurized coolant tube/catheter through which cryogenic fluid may pass until it exits the tube/catheter through a nozzle/hole/valve, thus entering the treated body lumen. Such nozzles/holes valves may be designed in any appropriate manner, such that the stream of cryogenic fluid exits into the body lumen, possibly directed at the treated region. According to one embodiment, as presented in FIG. 6A, inflow 133 exits tube 60 via hole (nozzle/orifice) 69*a*, which is an opening at the distal end of tube 60. It is noted, that although not illustrated, any one of the holes/nozzles described herein may include any type of valve or the like.

Figure 6A:
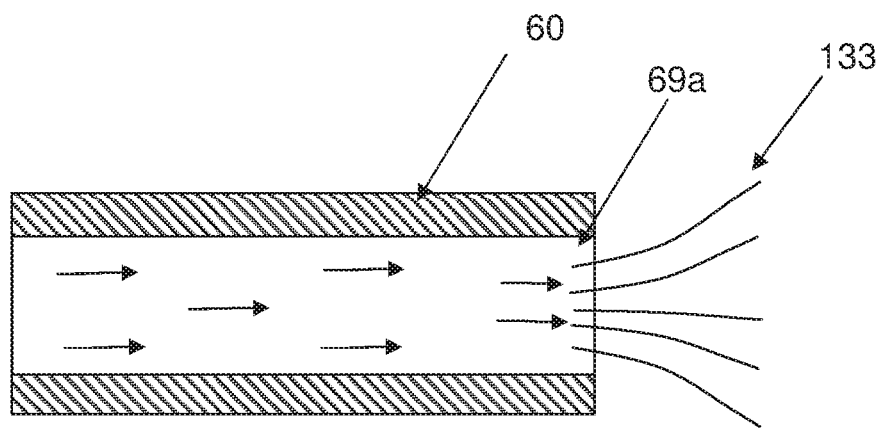
FIGS. 6A to 6E illustrate schematic lengthwise sectional views of the distal end of a cryotherapy device, which includes specific nozzles, providing different types of sprays, in accordance with some embodiments of the present invention.
Figure 6B:
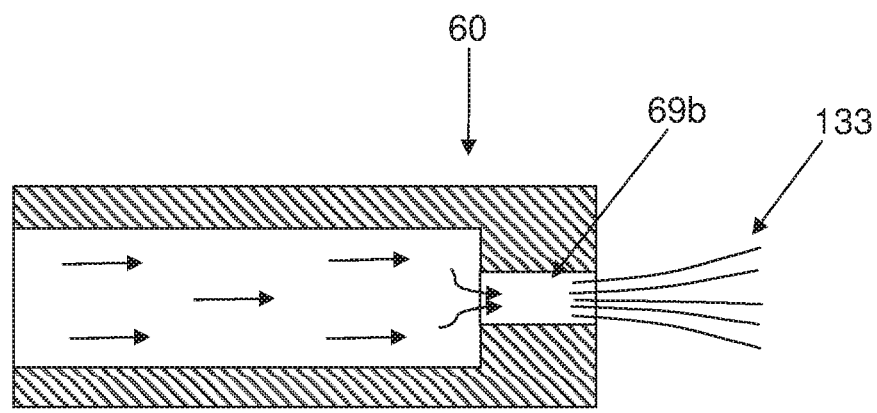

According to some embodiments, as presented in FIG. 6B, inflow 133 exits via a hole (nozzle/orifice) 69*b*, which has a reduced diameter in respect to the diameter of tube 60. Such a reduced diameter may provide cryogenic fluid sprayed at defined pressure onto the treated region and/or may enable a more efficient and accurate Joule Thompson effect.

According to some embodiments of the present invention, hole/nozzle/orifice/ 69*a* or 69*b*, as illustrated in FIGS. 6A and 6B, are aligned in the direction of tube 60 in order to result with frontal spray of inflow 133. According to other embodiments of the present invention, the hole/nozzle/orifice is directed in any appropriate direction, including on the side of tube 60. According to some embodiments, the direction of the spray exiting any one of the nozzles may be changed by an element in the nozzle that may be directed in any appropriate direction, wherein the direction of the element may be changed automatically, manually, by electronic means, in response to data received from any appropriate sensors, and the like.

Figure 6C:
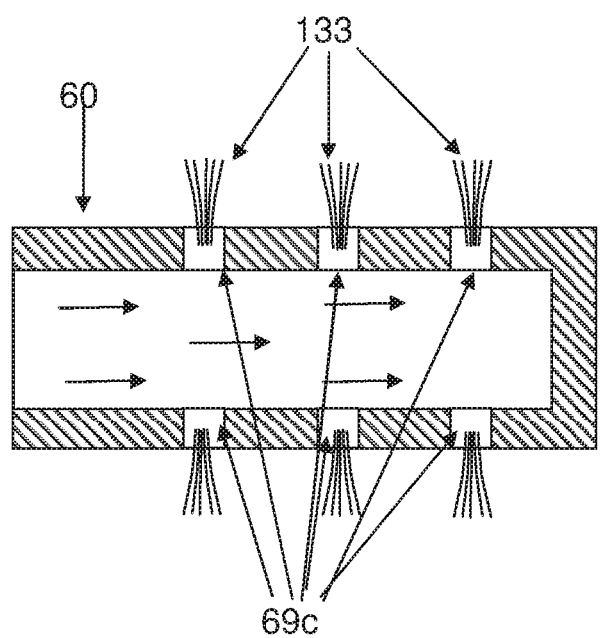

According to some embodiments, as illustrated in FIG. 6C, any number of holes in tube 60 may exist, allowing inflow 133 to exit through a number of holes 69*c*. Further, holes 69*c*, may be arranged in any desired configuration and further, may each include a valve that may be closed or opened or partially opened, as required.

Figure 6D:
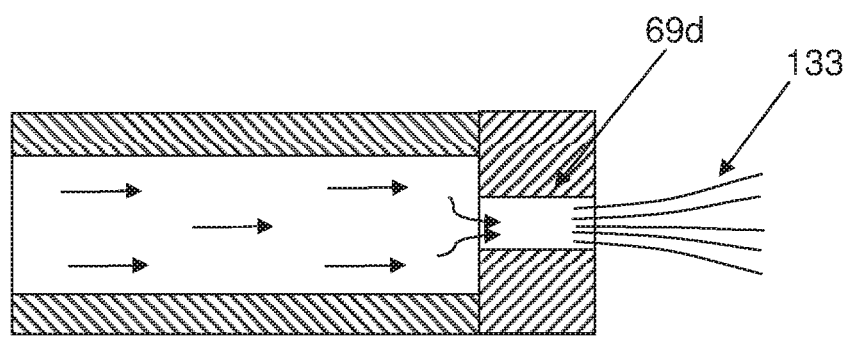
Figure 6E:
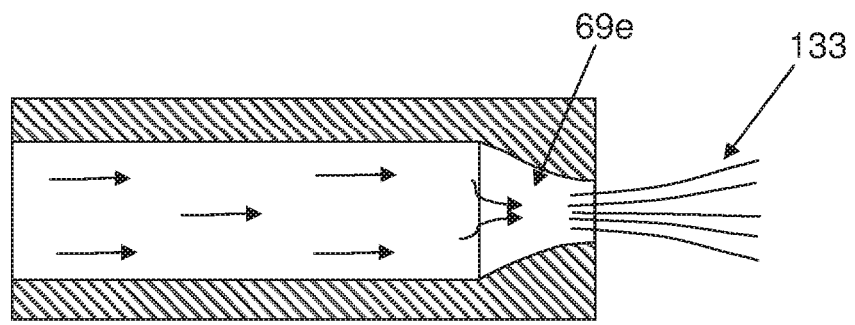

According to some embodiments, the nozzle is part of tube 60, according to other embodiments, as presented, e.g., in FIG. 6D, nozzle 69*d* is an additional component that is attached or connected to tube 60 by any appropriate means. This connection or attachment may result from fabrication advantages or constraints. According to some embodiments, any one of the nozzles may have a dedicated shape or size, for example, as illustrated in FIG. 6E, tapered nozzle 69*e* may be utilized. The size and shape of the nozzles, as well as the number of nozzles may be optimized according to each treatment, e.g., the size or type of the treated region/lesion, the size of the body lumen in which the treated region/lesion is found, the size and shape of an inflated cryo-balloon and the like. In order to achieve dedicated shape for nozzle 69*e*, additional process may be needed, such as thermal treatment or machining. The inner diameter of any one of the inflow or injection nozzles may be in the range of about 0.05-0.3 mm, while the inner diameter of any one of the evacuation or outflow nozzles may be in the range of about 0.5-4 mm in average. It is noted that the cross-section of the nozzle may be of any appropriate shape, including circular, non-circular, oval, slit-shaped, or the like Reference is now made to FIGS. 7A and 7B, which illustrate schematic transverse cross-sectional views of a cryotherapy device's distal end within an endoscope that has in-flow and out-flow channels, in accordance with some embodiments of the present invention. According to some embodiments, the cryotherapy device's distal end 24 directs the inflow 133 of coolant jet to the treated targeted region. The cryotherapy catheter is inserted from the proximal end of the endoscope through its in-flow channel.

According to some embodiments of the current invention, and as detailed in FIGS. 1 to 6, evacuation of the expanded coolant, as well as any other fluids present in the treated organ, is performed though a catheter/tube inserted into the organ via the endoscope. According to some embodiments, the evacuation may be performed through one or several inherent tubes or paths that may be part of the endoscope or that may be added thereto or fed therethrough. For example, some endoscopes have an opening at their back side (e.g. cystoscopic and hysteroscopic resectoscopes) where the cryotherapy device may be inserted. In such endoscopes at least part of the evacuation can take place through this back side (773) while some evacuation can be done through the out-flow exit (771) and/or through the in-flow entrance (772). It is further noted that the inflow, outflow and lumen pressure, affected by the inflow/outflow, may be controlled using such opening.

According to some embodiments of the present invention, the opening to the evacuation tubes/catheters may be in close proximity to or at the same or similar plane to inflow 133 (see, e.g., opening 77*a* as illustrated in FIG. 7A). According to other embodiments several circumferential side evacuation openings 77*b*, as illustrated in FIG. 7B, are provided. As detailed herein, the position, number, size, diameter, etc. of the evacuation tubes may be altered and may be defined as required. Further, any one of the openings may be fitted with a valve allowing the opening to be opened, closed or partially closed, such that any one of the openings may be used as required. The operation of the valves may be electronic, manual, automatic, according to signal received from any appropriate sensors and the like.

Reference is now made to FIGS. 8A and 8B, which illustrate schematic lengthwise sectional views of cryotherapy devices fed into the treated lumen through an endoscope, during ablation procedure in accordance with some embodiments of the present invention. The dedicated ablating component, 83*a* as illustrated in FIG. 8A or 83*b* as illustrated in FIG. 8B, may be an unfolded cryo balloon (as partially illustrated in FIG. 4E).

In order to treat targeted region 82 an ablating device 80 is inserted into endoscope 16 through its working channel in a way that device's distal end 24 exits the endoscope's distal end inside the body lumen 81, while device's proximal end 85 remains outside of the endoscope's proximal end and outside of the treated patient, as illustrated in FIG. 8A. According to some embodiments of the present invention, dedicated ablating component 83*a* is unfolded within body lumen 81 in order to treat targeted region 82, as illustrated in FIG. 8A.

According to other embodiments of the current invention, a broader ablating component 83*b* is unfolded within the body lumen 81 in order to treat targeted regions 82 and 82*b* and maybe more regions at the same time. Possibly the entire lumen may be treated if necessary.

Reference is now made to FIGS. 8C and 8D, which illustrate schematic lengthwise sectional views of a cryotherapy inflated device introduced via an endoscope within the treated lumen during an ablation procedure in accordance with some embodiments of the present invention. The inflated component may include several regions, each of which may have a different compliance. The inflated component may be constructed from non-compliant or semi-compliant part (0-8%), see element 83*c* as illustrated in FIGS. 8C and 8D, and semi-compliant or compliant part (5-200%), see element 83*d* as illustrated in FIGS. 8C and 8D. According to some embodiments, element 83*c* may be prepared from any appropriate type of metal or plastic. According to some embodiments, element 83*c* may have a folded and unfolded configuration.

According to some embodiments, the cold energy is transferred to the tissue via compliant/semi-compliant element 83*d*. As shown in the figures, according to some embodiments, only a certain part of the cryo-balloon may come in contact with the treated area, while other regions in the treated lumen are not in direct contact with the cryo-balloon. Element 83*d* may be an inflatable component, wherein element 83*c* may be a structured element designed to hold and/or partially define the shape of element 83*d*. The inflated component 83*d* may be kept unfolded while within endoscope 16 (FIG. 8C) and its shape is such that when inflated (by inflow 133 or other means), element 83*d* is directed toward the targeted area, transferring cold energy thereto.

Reference is now made to FIGS. 8E to 8G, which illustrate schematic lengthwise sectional views of a cryotherapy inflated device introduced inside lumen during an ablation procedure in accordance with some embodiments of the present invention. FIG. 8E illustrates the inflated component inside the lumen close to the treated area 82*c*, having an active part 83*d*. FIG. 8F illustrates inflated component with low compliance (0-8%) active region 83*d*1, while FIG. 8G illustrates inflated component with high or semi compliance (5-200%) active region 83*d*2. As illustrated in the figures, use of a high or semi compliance inflated element may result with optimal fitting of the device to the treated area, since the contact of the device with the treated area is optimal.

Figure 9A:
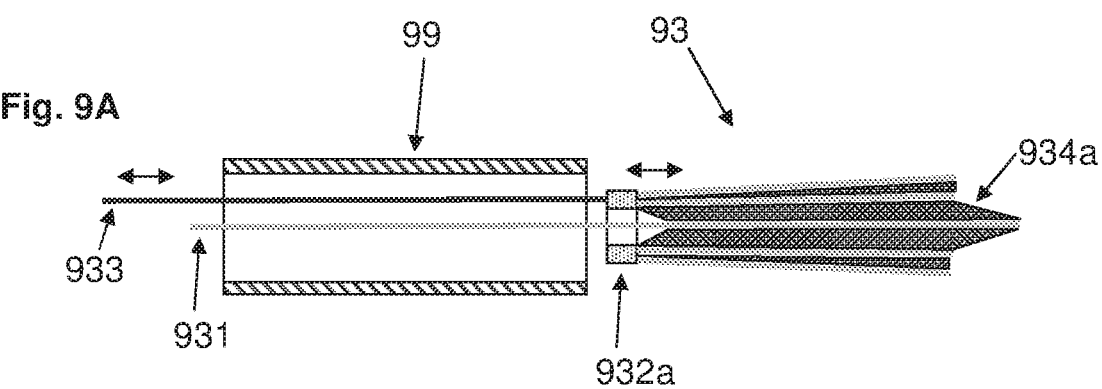
FIGS. 9A and 9B illustrate schematic lengthwise sectional views of the distal end of a cryotherapy device, specifically presenting cryo-balloons, in accordance with some embodiments of the present invention.
Figure 9B:
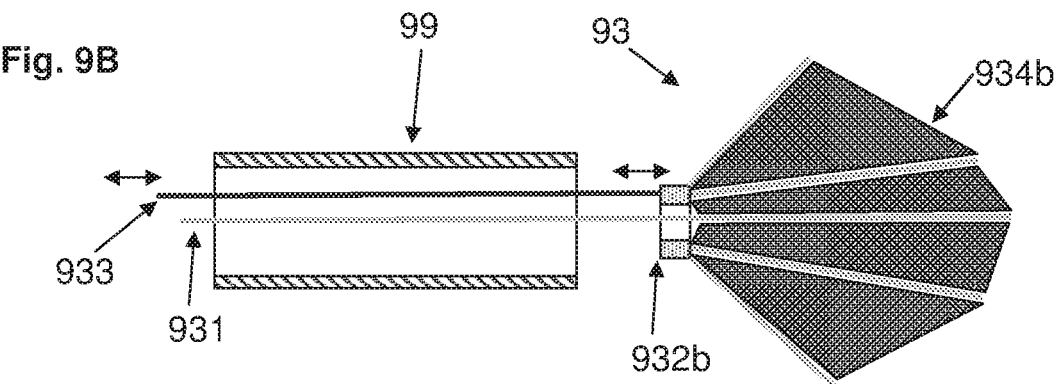

Reference is now made to FIGS. 9A and 9B, which illustrate schematic lengthwise sectional views of an ablation device's distal end 93 in accordance with some embodiments of the present invention. According to some embodiments, unfolded distal end 934*a*, which is illustrated in FIG. 9A, may comprise supporting ribs as well as a cryo-balloon components. According to some embodiments of the current invention, unfolded distal end 934*a* is inserted into the body lumen through sheath 99 (which may be the endoscope's working channel itself) by pushing catheter or wire 931. While the ablating distal end 934*a* is positioned within the body lumen in the proximity of the targeted region (see FIGS. 8A and 8B), user may manipulate bar (or lever, valve, faucet or controller) 933, in order to unfold the ablating distal end 934*b* as illustrated in FIG. 9B, and then activate the ablating mechanism (RF and/or Cryo).

Some embodiments of the invention are directed to RFA devices and ablation methods, wherein a folded RF mesh may be introduced via an endoscope to be unfolded within a body lumen to treat a targeted area. For example, the cryo-balloon presented in FIGS. 8A-D and 9A-B may be replaced by arm RF mesh.

The preceding specific embodiments are illustrative of the practice of the techniques of this disclosure. It is to be understood, therefore, that other expedients known to those skilled in the art or disclosed herein may be employed without departing from the scope of the following claims.

What is claimed is:

1. A cryotherapy device for treating a body lumen having limited natural evacuation capacity of gasses, comprising:
   at least one inflow channel for providing expandable cryo-fluid to a distal end of said cryotherapy device;
   at least one element, located at said distal end of said cryotherapy device and defines a channel between said inflow channel and said body lumen, configured for selectively directing said expandable cryo-fluid from said distal end of said cryotherapy device to a targeted area in said body lumen, wherein said at least one element is suitable for expansion of said expandable cryo-fluid when exiting from said cryotherapy device into said body lumen;
   at least one outflow channel comprising at least one opening into said body lumen, and at least one opening outside the body;
   a controller for controlling the providing of said expanded cryo-fluid into the body lumen and the evacuation of said expanded cryo-fluid from said body lumen;
   wherein the controller is configured to receive signals indicative of pressure in said body lumen and to control said providing and/or said evacuation of said expanded cryo-fluid according to said received signals to maintain pressure levels between 10 mBar and 100 mBar in said body lumen; and
   wherein the cryotherapy device has an overall diameter between 0.8-9 mm and is shaped to be introduced into the body lumen via an endoscope.

2. The cryotherapy device according to claim 1, wherein said body lumen comprises a bladder.

3. The cryotherapy device according to claim 2, wherein said at least one inflow channel and said outflow channel are at least partially bendable and kink-resistant to allow angulation of said cryotherapy device within said bladder.

4. The cryotherapy device according to claim 2, wherein the inflow channel and the outflow channel are the same channel.

5. The cryotherapy device according to claim 2, wherein the inflow channel, the outflow channel, or both, is formed of a material that is at least partially braided, coiled, or both.

6. The cryotherapy device according to claim 2, wherein the inflow channel is attached to at least one inflow nozzle, and wherein the inner diameter of any one of the inflow nozzles is in the range of 0.05-0.3 mm.

7. The cryotherapy device according to claim 2, wherein the outflow channel is attached to at least one outflow opening, and wherein the inner diameter of any one of the outflow openings is in the range of 0.5-4.0 mm.

8. The cryotherapy device according to claim 2, comprising at least one sensor configured to gather data regarding pressure within said bladder.

9. The cryotherapy device according to claim 8, wherein said controller is configured to stop injection of said expandable cryo-fluid into said bladder if a pressure within said bladder is above a preset of pressure between 30 mBar and 100 mBar.

10. The cryotherapy device according to claim 2, comprising at least one sensor configured to gather data regarding temperature within said bladder.

11. The cryotherapy device according to claim 10, wherein said controller is configured to stop injection of said expandable cryo-fluid into said bladder if a temperature within the bladder is below 10 degrees Celsius.

12. The cryotherapy device according to claim 2, wherein said at least one element comprises a nozzle configured to spray said expandable cryo-fluid onto a treated region within said bladder and/or surroundings of said target area.

13. The cryotherapy device according to claim 1, wherein said body lumen is a cervix, a prostate, a urethra, a ureter or a uterus.

14. The cryotherapy device according to claim 1, wherein said at least one inflow channel and said outflow channel are at least partially bendable and kink-resistant to allow angulation of said cryotherapy device within said body lumen.

15. The cryotherapy device according to claim 14, wherein said angulation comprises angulation larger than 90 degrees.

16. The cryotherapy device according to claim 1, wherein said expandable cryo-fluid comprises one or more of liquid nitrogen, carbon dioxide, and nitrous oxide.

17. The cryotherapy device according to claim 1, wherein said at least one inflow channel provides at least one chemical and/or biological therapeutic agent.

18. A cryotherapy device according to claim 1, wherein said controller is configured to receive signals indicative of pressure accumulation in said lumen having limited natural evacuation of gasses, and to control said providing and said evacuation of said expanded cryo-fluid according to said received signals, thereby reducing damage to tissue in said body lumen due to said pressure accumulation.

19. A cryotherapy device for treating a bladder comprising:
   at least one inflow channel for providing expandable cryo-fluid to a distal end of said cryotherapy device;
   at least one element, located at said distal end of said cryotherapy device and defines a channel between said inflow channel and said bladder, configured for selectively directing said expandable cryo-fluid from said distal end of said cryotherapy device to a targeted area in said bladder, wherein said at least one element is suitable for expansion of said expandable cryo-fluid when exiting from said cryotherapy device into said bladder;
   at least one outflow channel comprising at least one opening into said bladder, and at least one opening outside the body;
   a controller for controlling the providing of said expanded cryo-fluid into the bladder and the evacuation of said expanded cryo-fluid from said bladder to maintain pressure levels between 10 mBar and 100 mBar in said bladder;
   wherein the controller is configured to receive signals indicative of blockage of said at least one outflow channel and to control said providing of said expanded cryo-fluid according to said received signals; and
   wherein the cryotherapy device is configured to be introduced into the bladder via a urethra.

20. A cryotherapy device according to claim 19, wherein said received signals indicate pressure in said body lumen, and wherein said controller is configured to control said providing of said expanded cryo-fluid according to said received signals, thereby reducing damage to tissue in said body lumen due to said blockage by accumulation of pressure in said body lumen.

* * * * *